US010604553B2

(12) United States Patent
Heo et al.

(10) Patent No.: US 10,604,553 B2
(45) Date of Patent: Mar. 31, 2020

(54) METHOD FOR FORMING A REVERSIBLE PROTEIN NANOCLUSTER USING LIGHT IN A CELL

(71) Applicant: KOREA ADVANCED INSTITUTE OF SCIENCE AND TECHNOLOGY, Daejeon (KR)

(72) Inventors: Won Do Heo, Daejeon (KR); Sang Kyu Lee, Seoul (KR); Hye Rim Park, Gimhae-si (KR)

(73) Assignee: Korean Advanced Institute of Science and Technolog, Daejeon (KR)

( * ) Notice: Subject to any disclaimer, the term of this patent is extended or adjusted under 35 U.S.C. 154(b) by 180 days.

(21) Appl. No.: 15/618,770

(22) Filed: Jun. 9, 2017

(65) Prior Publication Data

US 2017/0275346 A1    Sep. 28, 2017

Related U.S. Application Data

(63) Continuation of application No. 14/348,757, filed as application No. PCT/KR2012/007927 on Sep. 28, 2012, now Pat. No. 9,708,381.

(30) Foreign Application Priority Data

Sep. 30, 2011 (KR) .......... 10-2011-0100334
Dec. 7, 2011 (KR) .......... 10-2011-0130081

(51) Int. Cl.
*C07K 14/47* (2006.01)
*C07K 14/325* (2006.01)
*C07K 14/415* (2006.01)
*C12N 9/00* (2006.01)
*C12N 9/12* (2006.01)
*C12N 13/00* (2006.01)
*G01N 33/58* (2006.01)
*G01N 33/68* (2006.01)

(52) U.S. Cl.
CPC ........ *C07K 14/4728* (2013.01); *C07K 14/325* (2013.01); *C07K 14/415* (2013.01); *C12N 9/12* (2013.01); *C12N 9/93* (2013.01); *C12N 13/00* (2013.01); *C12Y 207/11017* (2013.01); *G01N 33/582* (2013.01); *G01N 33/6845* (2013.01); *C07K 2319/60* (2013.01); *C07K 2319/735* (2013.01)

(58) Field of Classification Search
None
See application file for complete search history.

*Primary Examiner* — Anand U Desai
(74) *Attorney, Agent, or Firm* — Ladas & Parry LLP

(57) ABSTRACT

To efficiently analyze interaction and function between proteins, the present invention relates to a method for forming a light-induced protein nanocluster, comprising: an expression vector preparation step of preparing a first expression vector including polynucleotides coding a first fusion protein including a light-induced heterodimer-forming protein and a first self-assembly protein, and a second expression vector including polynucleotides coding a couple protein that forms a homodimer with said light-induced heterodimer-forming protein, or a second fusion protein including said couple protein and a second self-assembly protein; a transformed cell, tissue or individual preparation step of transforming cells, tissues or individuals using said first expression vector and second expression vector; and a light radiation step of radiating light having a wavelength for inducing the formation of heterodimer between said light-induced heterodimer-forming protein and said couple protein, to said transformed cells, tissue or individuals.

7 Claims, 19 Drawing Sheets
Specification includes a Sequence Listing.

SAP: self-assembled protein
CIBN: N-terminal fragment of CIB1 protein
PHR: N-terminal fragment of chryptochrome2 (CRY2), homodimerizable SAP self-assembled protein
⟵⟶ protein-protein interaction

```
                        SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: tetracystein motif
<220> FEATURE:
<221> NAME/KEY: MOD_RES
<222> LOCATION: 3-4
<223> OTHER INFORMATION: Xaa=any amino acid

<400> SEQUENCE: 1

Cys Cys Xaa Xaa Cys Cys
1               5
```

METHOD FOR FORMING A REVERSIBLE PROTEIN NANOCLUSTER USING LIGHT IN A CELL

FIELD OF THE INVENTION

The present application claims benefit of priority of Korean Patent Application Nos. 2011-0100334 and 2011-0130081 filed Sep. 30, 2011 and Dec. 7, 2011, respectively. The documents are herein incorporated by reference in its entirety.

The present invention relates to a method for forming a reversible protein nanocluster, more particularly to a method for forming a reversible protein nanocluster using light in a cell and a method for inhibiting function of a protein reversibly.

BACKGROUND OF THE INVENTION

The dynamic interactions between varieties of biologically active substances regulate various physiological functions, and diseases are caused in an unusual situation when these interactions occur improperly or the interaction between molecules which should not interact each other occurs. In general, two proteins having complementary structure interact and bioactive compounds interact specific parts of tertiary structure of the proteins. These bioactive compounds may be therapeutic candidates for diagnosing, preventing, treating or alleviating diseases involved in the proteins by modulating the function of the target proteins. Studies on screening the disease targets or therapeutics for the disease have been sustained by analyzing the interaction between these proteins and the interactions between proteins and small-molecule compounds.

For example, various techniques such as phage display (Sche et al., Chem. Biol., 6: 707, 1999), yeast two/three-hybrid analysis (Licitra et al., Proc. Natl. Acad. Sci. USA 93: 12817, 1996), and parallel analysis of yeast strain having deletions heterologous (Zheng et al., Chem. Biol., 11: 609, 2004) have been suggested. However, these techniques have problems, such as high background, false positive and low sensitivity of the reaction and with in vitro experiment or reactions using non-mammalian cells make it hard to convince the experimental result.

In addition, inducing a deletion or a mutation of the gene encoding a protein or treating specific inhibitor for the protein to the cell or the subject expressing the protein are used to observe the physiochemical changes in the cell or the subject.

Among these methods, U.S. Pat. No. 5,270,163 discloses a method for screening specific biomolecules that bind specifically to single-stranded oligonucleotides, the so-called aptamer. Lunder et al. discloses a method of screening target-binding motif using phage display (Lunder et al., Appl. Biochem. Biotechnol., 127 (2): 125-131, 2005). U.S. Patent Publication No. 2010-0143371 discloses a method for inhibiting the function of the proteins in the cell using an intrabody which is a variable domain of kappa chain of human antibodies that specifically bind to intracellular proteins.

DETAILED DESCRIPTION OF THE INVENTION

Technical Problems

However, those methods for analyzing protein interaction have disadvantages in that the methods are not performed in real time and cannot eliminate the possibility of false positive or false-negative as well as they are inefficient in that introducing specific mutations or screening specific inhibitor for proteins are cost and time-consuming process. Moreover, the treatment of the specific inhibitor causes irreversible protein inactivation and thus it is difficult to analyze function of proteins essential for cell survival using the specific inhibitor.

The present invention intended to solve several problems, including the above-mentioned problems, the purpose of the present invention is to provide a method of forming reversible protein nano-cluster in cells using light.

In addition, the other purpose of the present invention is to provide a method for analyzing inter-protein interaction and a kit using the method for forming reversible protein nano-cluster.

Furthermore, another purpose of the present invention is to provide methods and kits for inhibiting a target protein in a cell or a subject using the formation of light-induced protein nano-cluster. However, these purposes are to be exemplary and the scope of the present invention is not limited thereto.

SUMMARY OF THE INVENTION

In an aspect to the present invention, an expression vector comprising a polynucleotide encoding a fusion protein including a light-induced heterodimerized protein and a self-assembled protein is provided.

According to the expression vector, the light-induced heterodimerized protein may be CIB, CIBN, PhyB, PIF, FKF1, GIGANTEA, CRY, or PHR.

According to the expression vector, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). The description for the self-assembled protein is applied to a first self-assembled protein and a second self-assembled protein which will be described later.

According to the expression vector, the fusion protein may contain a fluorescent protein, and the fluorescent protein may be added to the N-terminus or the C-termius of the fusion protein or the fluorescent protein may be inserted between the light-induced dimerizing protein and the self-assembled protein. The fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP (enhanced green fluorescent protein), Emerald (Tsien, Annu. Rev. Biochem., 67: 509-544, 1998), Superfolder (Pedelacq et al., Nat. Biotech., 24: 79-88, 2006), GFP (Prendergast et at, Biochem., 17 (17): 3448-3453, 1978), Azami Green (Karasawa, et al., J. Biol. Chem., 278: 34167-34171, 2003), TagGFP (Evrogen, Russia), TurboGFP (Shagin et al., Mol. Biol. Evol., 21 (5): 841-850, 2004), ZsGreen (Matz et al., Nat. Biotechnol., 17: 969-973, 1999) or T-Sapphire (Zapata-Hommer et at, BMC Biotechnol., 3:5, 2003). The yellow fluorescent protein may be EYFP (enhanced yellow fluorescent protein, Tsien, Annu. Rev. Biochem., 67: 509-544, 1998), Topaz (Hat et al., Ann. NY Acad. Sci., 1: 627-633, 2002), Venus (Nagai et al., Nat. Biotechnol., 20(1): 87-90, 2002), mCitrine (Griesbeck et al., J. Biol. Chem., 276: 29188-29194, 2001), Ypet (Nguyet and Daugherty, *Nat. Biotechnol.*, 23(3): 355-360, 2005), TagYFP (Evrogen, Russia), PhiYFP (Shagin et al., *Mol. Biol. Evol.*, 21(5): 841-850, 2004), ZsYellow1 (Matz et al., *Nat. Biotechnol.*, 17: 969-973, 1999), or mBanana (Shaner et al., *Nat. Biotechnol.*, 22: 1567-1572, 2004). The red fluorescent protein may be mRuby (Kredel et al., *PLoS ONE*, 4(2): e4391, 2009), mApple (Shaner et al., *Nat. Methods*, 5(6): 545-551, 2008), mStrawberry (Shaner et al., *Nat. Biotechnol.*, 22: 1567-1572, 2004) and AsRed2 (Shanner et at, *Nat. Biotechnol.*, 22: 1567-1572, 2004) or mRFP (Campbell et al., *Proc. Natl. Acad. Sci. USA*, 99(12): 7877-7882, 2002). The orange fluorescent protein may be Kusabira Orange (Karawawa et al., *Biochem. J.* 381(Pt 1): 307-312, 2004), Kusabira Orange2 (MBL International Corp., Japan), mOrange (Shaner et al., *Nat. Biotechnol.*, 22: 1567-1572, 2004), mOrange2 (Shaner et al., *Nat. Biotechnol.*, 22: 1567-1572, 2004), dTomato (Shaner et al., *Nat. Biotechnol.*, 22: 1567-1572, 2004), dTomato-Tandem (Shaner et al., *Nat. Biotechnol.*, 22: 1567-1572, 2004), TagRFP (Merzlyak et al., *Nat. Methods*, 4(7): 555-557, 2007), TagRFP-T (Shaner et al., *Nat. Methods*, 5(6): 545-551, 2008), DsRed (Baird et al., *Proc. Natl. Acad. Sci. USA*, 97: 11984-11989, 1999), DsRed2 (Clontech, USA), DsRed-Express (Clontech, USA), DsRed-Monomer (Clontech, USA), or mTangerine (Shaner et al., *Nat Biotechnol*, 22: 1567-1572, 2004 above). The cyan fluorescent protein may be ECFP (enhanced cyan fluorescent protein, Cubitt et al., *Trends Biochem. Sci.*, 20: 448-455, 1995), mECFP (Ai et al., *Biochem. J.*, 400(3): 531-540, 2006), mCerulean (Koushik et al., *Biophys. J.*, 91(12): L99-L101, 2006), CyPet (Nguyet and Daugherty, *Nat. Biotechnol.*, 23 (3): 355-360, 2005), AmCyan1 (Matz et al., *Nat. Biotechnol.*, 17: 969-973, 1999), Midori-Ishi Cyan (Karawawa et al., *Biochem. J.*, 381(Pt 1): 307-312, 2004), TagCFP (Evrogen, Russia) or mTFP1, (Ai et at, *Biochem. J.*, 400 (3): 531-540, 2006). The blue fluorescent protein may be EBFP (enhanced blue fluorescent protein, Clontech, USA), EBFP2 (Ai et al., *Biochemistry*, 46 (20): 5904-5910, 2007), Azurite (Mena et al., *Nat. Biotechnol.*, 24: 1569-1571, 2006) or mTagBFP (Subach et al., *Chem. Biol.*, 15(10): 1116-1124, 2008). The far red fluorescent protein may be mPlum (Wang et al., *Proc. Natl. Acad. Sci. USA*, 101: 16745-16749, 2004), mCherry (Shanner et al., *Nat. Biotechnol.*, 22: 1567-1572, 2004), dKeima-Tandem (Kogure et al., *Methods*, 45(3): 223-226, 2008), JRed (Shagin et al., *Mol. Biol. Evol.*, 21(5): 841-850, 2004), mRaspberry (Shanner et al., *Nat. Biotechnol.*, 22: 1567-1572, 2004), HcRed1 (Fradkov et al., *Biochem. J.*, 368(Pt 1): 17-21, 2002), HcRed-Tandem (Fradkov et al., *Nat. Biotechnol.*, 22(3): 289-296, 2004), AQ143 (Shkrob et al., *Biochem. J.*, 392: 649-654, 2005). The tetracysteine fluorescent motif may be a polypeptide including an amino acid sequence of Cys-Cys-Xaa-Xaa-Cys-Cys (SEQ ID NO: 1), wherein the Xaa is any one amino acid except cysteine. The description for the fluorescent proteins applied to a first fluorescent protein, a second fluorescent proteins, a third fluorescent protein and a fourth fluorescent protein which will be described later in a same manner.

In another aspect to the present invention, a kit for forming light-induced protein nano-clusters comprising a first expression vector including a polynucleotide encoding a first fusion protein comprising a light-induced heterodimerized protein and a first self-assembled protein; and a second expression vector including a polynucleotide encoding a partner protein capable of forming a heterodimer with the light-induced heterodimerizing protein, or a second fusion protein containing the partner protein and a second self-assembled protein is provided.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the kit, at least one among the first fusion protein, the partner protein and the second fusion protein may further comprise a fluorescent protein and the fluorescent protein may be added to N-termius or C-terminus of the first fusion protein, the partner protein and/or the second fusion protein or may be inserted between the light-induced heterodimerized protein and the first self-assembled protein or between the partner protein and the second self-assembled protein. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

In another aspect to the present invention, a method for forming a protein nano-cluster is provided, wherein the method comprises: providing a first expression vector including a polynucleotide encoding a first fusion protein comprising a light-induced heterodimerized protein and a first self-assembled protein, and a second expression vector including a polynucleotide encoding a partner protein capable of forming a heterodimer with the light-induced heterodimerizing protein, or a second fusion protein containing the partner protein and a second self-assembled protein;

transforming a cell, a tissue or a subject with the first expression vector and the second expression vector;

irradiating light having wavelength capable of indcucing heterodimerization between the light-induced heterodimerized protein and the partner protein to the cell, the tissue or the subject.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the kit, at least one among the first fusion protein, the partner protein and the second fusion protein may further comprises a fluorescent protein and the fluorescent protein may be added to N-termius or C-terminus of the first fusion protein, the partner protein and/or the second fusion protein or may be inserted between the light-induced heterodimerized protein and the first self-assembled protein or between the partner protein and the second self-assembled protein. The fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

In another aspect to the present invention, a method for analyzing interaction between proteins using light-induced nano-cluster formation is provided, wherein the method comprises: expressing 1) a first fusion protein comprising a first self-assembled protein, a first fluorescent protein and a light-induced heterodimerized protein, 2) optionally a second fusion protein comprising a second fluorescent protein and a second self-assembled protein, 3) a third fusion protein comprising a third fluorescent protein, 4) a partner protein capable of heterodimerizing with light-induced heterodimerized protein by light irradiating, 5) a bait protein, and 6) a target protein being analyzed whether it interacts with the bait protein or not in a cell at the same time, wherein the partner protein is incorporated to the second fusion protein or the third fusion protein, the bait protein is incorporated to one of the second fusion protein, the third protein and the fourth fusion protein containing the first self-assembled protein and the first fluorescent protein, and the target protein is incorporated to one of other fusion proteins except the fusion protein containing the bait protein or a fifth fusion protein comprising a fourth fluorescent protein;

irradiating light having wavelength capable of indcucing heterodimerization between the light-induced heterodimerized protein and the partner protein to the cell; and observing the pattern and intensity of fluorescence of the fluorescent proteins, with the proviso the second fluorescent protein may be omitted in case that light-induced heterodimerized protein or the partner protein forms a homodimer regardless of light irradiating, wherein all the fluorescent proteins emit different wavelengths of light, and wherein the first self-assembled protein or the second self-assembled protein may be omitted form any fusion proteins containing DsRed when either the first fluorescent protein or the second fluorescent protein is DsRed.

According to the method, the first fluorescent to the fourth fluorescent protein may be independently green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

In another aspect to the present invention, a method for analyzing interaction between proteins using light-induced nano-cluster formation is provided, wherein the method comprises: expressing 1) a first fusion protein comprising a first self-assembled protein, a first fluorescent protein and a light-induced heterodimerized protein, 2) optionally a second fusion protein comprising a second fluorescent protein and a second self-assembled protein, 3) a third fusion protein comprising a third fluorescent protein, 4) a partner protein capable of heterodimerizing with light-induced heterodimerized protein by light irradiating, 5) a bait protein, and 6) a target protein interacting with the bait protein in a cell at the same time, wherein the partner protein is incorporated to the second fusion protein or the third fusion protein, the bait protein is incorporated to one of the second fusion protein, the third protein and the fourth fusion protein containing the first self-assembled protein and the first fluorescent protein, and the target protein is incorporated to one of other fusion proteins except the fusion protein containing the bait protein or a fifth fusion protein comprising a fourth fluorescent protein;

treating a candidate substance capable of controlling the interaction between the bait protein and the target protein to the cell;

irradiating light having wavelength capable of indcucing heterodimerization between the light-induced heterodimerized protein and the partner protein to the cell before, after or at the same time of treating the candidate substance to the cell; and observing the pattern and intensity of fluorescence of the fluorescent proteins, with the proviso that the second fluorescent protein may be omitted in case that light-induced heterodimerized protein or the partner protein forms a homodimer regardless of light irradiating, wherein all the fluorescent proteins emit different wavelengths of light, and wherein the first self-assembled protein or the second self-assembled protein may be omitted from any fusion proteins containing DsRed when either the first fluorescent protein or the second fluorescent protein is DsRed.

According to the method, the first fluorescent to the fourth fluorescent protein may be independently green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

In another aspect of the present invention, a kit for analyzing interaction between proteins is provided, wherein the kit comprises:

a first expression vector including a first gene construct containing a promoter and a polynucleotide encoding a first fusion protein comprising a first self-assembled protein, a first fluorescent protein and a light-induced heterodimerized protein, wherein the polynucleotide is operably linked to the promoter;

optionally a second expression vector including a second gene construct containing a promoter and a polynucleotide encoding a second fusion protein comprising a second fluorescent protein and a second self-assembled protein, wherein the polynucleotide is operably linked to the promoter;

a third expression vector including a third gene construct containing a promoter and a polynucleotide encoding a third fusion protein comprising a third fluorescent protein, wherein the polynucleotide is operably linked to the promoter; and optionally a fourth expression vector including a fourth gene construct containing a promoter and a polynucleotide encoding a fourth fusion protein containing the first self-assembled protein, the first fluorescent protein and a bait protein, wherein the polynucleotide is operably linked to the promoter, wherein the bait protein is incorporated to one of the second fusion protein and the third fusion protein when the fourth expression vector is omitted, and one of the second fusion protein and the third fusion protein contains a partner protein capable of heterodimerizing with light-induced heterodimerized protein by light irradiating, one lacking the bait protein among the second fusion protein and the third fusion protein or a fifth expression vector optionally expressed which comprises a fifth fusion protein comprising a fourth fluorescent protein contains a target protein which is a subject to be examined whether it interacts with the bait protein or not, with the proviso that the second fluorescent protein may be omitted in case that light-induced heterodimerized protein or the partner protein forms a homodimer regardless of light irradiating, wherein all the fluorescent proteins emit different wavelengths of light, and wherein the first self-assembled protein or the second self-assembled protein may be omitted from any fusion proteins containing DsRed when either the first fluorescent protein or the second fluorescent protein is DsRed.

According to the kit, the first fluorescent to the fourth fluorescent protein may be independently green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

In another aspect of the present invention, a kit for analyzing interaction between proteins is provided, wherein the kit comprises:

a first expression vector including a first gene construct containing a promoter and a first polynucleotide encoding a first fusion protein comprising a first self-assembled protein, a first fluorescent protein and a light-induced heterodimerized protein, wherein the polynucleotide is operably linked to the promoter;

optionally a second expression vector including a second gene construct containing a promoter and a second polynucleotide encoding a second fusion protein comprising a second fluorescent protein and a second self-assembled protein, wherein the second polynucleotide is operably linked to the promoter;

a third expression vector including a third gene construct containing a promoter and a third polynucleotide encoding a third fusion protein comprising a third fluorescent protein, wherein the third polynucleotide is operably linked to the promoter; and optionally a fourth expression vector including a fourth gene construct comprising a fourth polynucleotide encoding a fourth fusion protein containing the first self-assembled protein and the first fluorescent protein and a multicloning site for inserting a polynucleotide encoding a bait protein to the fourth polynucleotide, wherein the polynucleotide encoding a bait protein is linked operably to the fourth polyncleotide, wherein the multicloning site is incorporated to one of the second expression vector and the third expression when the fourth expression vector is omitted, and one of the second fusion protein and the third fusion protein contains a partner protein capable of heterodimerizing with light-induced heterodimerized protein by light irradiating, an wherein one lacking the multicloning site for inserting a polynucleotide encoding a bait protein among the second expression vector and the third expression vector or an optionally expressed fifth expression vector including a fifth polynucleotide encoding a fifth fusion protein comprising a fourth fluorescent protein contains a multicloning site for inserting a polynucleotide encoding a target protein which is a subject to be examined whether it interacts with the bait protein or not, with the proviso that the second fluorescent protein may be omitted in case that light-induced heterodimerized protein or the partner protein forms a homodimer regardless of light irradiating, wherein all the fluorescent proteins emit different wavelengths of light, and wherein the first self-assembled protein or the second self-assembled protein may be omitted when either the first fluorescent protein or the second fluorescent protein is DsRed.

According to the kit, the first fluorescent to the fourth fluorescent protein may be independently green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

In another aspect of the present invention, a method for inhibiting a target protein reversibly using light-induced protein nano-cluster formation is provided, wherein the method comprises: expressing a fusion protein comprising a self-assembled protein and a light-induced heterodimerized protein, a partner protein capable of heterodimerizing with light-induced heterodimerized protein and a bait protein interacting with a target protein in a cell or a subject expressing the target protein as an inherent protein; and Inducing a protein nano-cluster formation by irradiating light having wavelength capable of inducing heterodimerizing between the light-induced heterodimerized protein and the partner protein to the cell or the subject.

According to the method, the self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the method, at least one protein among the fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may be homodimerized regardless of light irradiation. In this case the light-induced heterodimerized protein or the partner protein capable of forming homodimer regardless of light irradiation may be CRY or PHR.

In another aspect of the present invention, a method for inhibiting a target protein reversibly using light-induced protein nano-cluster formation is provided, wherein the method comprises: co-expressing a first fusion protein comprising a first self-assembled protein and a light-induced heterodimerized protein, a second fusion protein comprising a second self-assembled protein and a partner protein capable of heterodimerizing with light-induced heterodimerized protein and a bait protein interacting with a target protein in a cell or a subject expressing the target protein as an inherent protein; and inducing a protein nano-cluster formation by irradiating light having wavelength capable of inducing heterodimerizing between the light-induced heterodimerized protein and the partner protein to the cell or the subject, wherein the bait protein is expressed as a fusion protein with the first self-assembled protein or the second self-assembled protein.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the method, at least one protein among the first fusion protein, the second fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may be homodimerized regardless of light irradiation. In this case the light-induced heterodimerized protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter and a second polynucleotide encoding a partner protein capable of heterodimerizing with light-induced heterodimerized protein, wherein the second polynucleotide is operably linked to the promoter, and a third expression vector including a third gene construct containing a promoter and a third polynucleotide encoding a bait protein interacting with the target protein, wherein the third polynucleotide is operably linked to the promoter, wherein the bait protein is expressed as a fusion protein with the self-assembled protein or the partner protein.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the first fusion protein, the second fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may be homodimerized regardless of light irradiation. In this case the light-induced heterodimerized protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a first fusion protein comprising a first self-assembled protein and a light-induced heterodimerized protein, wherein the first polynucleotide is operably linked to the promoter; a second expression vector including a second gene construct containing a promoter and a second polynucleotide encoding a second fusion protein comprising a second self-assembled protein and a partner protein capable of heterodimerizing with the light-induced heterodimerized protein, wherein the second polynucleotide is operably linked to the promoter; and a third expression vector including a third gene construct containing a promoter and a multicloning site for inserting a third polynucleotide encoding a bait protein interacting with the target protein, wherein the third polynucleotide is operably linked to the promoter, wherein the bait protein is expressed as a fusion protein with the self-assembled protein or the partner protein.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the first fusion protein, the second fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may be homodimerized regardless of light irradiation. In this case the light-induced heterdimerizable protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter, a second expression vector including a second gene construct containing a promoter and a second polynucleotide encoding a partner protein capable of heterodimerizing with the light-induced heterodimerized protein, wherein the second polynucleotide is operably linked to the promoter; and a third expression vector including a third gene construct containing a promoter and a multicloning site for inserting a third polynucleotide encoding a bait protein interacting with the target protein, wherein the third polynucleotide is operably linked to the promoter, wherein the bait protein is expressed as a fusion protein with the self-assembled protein or the partner protein.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to kit, the light-induced heterodimerized protein or the partner protein may be homodimerized regardless of light irradiation. In this case, the light-induced heterodimerized protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a first fusion protein comprising a first self-assembled protein and a light-induced heterodimerized protein, wherein the first polynucleotide is operably linked to the promoter; a second expression vector including a second gene construct containing a promoter and a second polynucleotide encoding a second fusion protein comprising a second self-assembled protein and a partner protein capable of heterodimerizing with the light-induced heterodimerized protein, wherein the second polynucleotide is operably linked to the promoter; and a third expression vector including a third gene construct comprising a promoter and a third polynucleotide encoding a bait protein interacting with the target protein, wherein the third polynucleotide is operably linked to the promoter, wherein the bait protein is expressed as a fusion protein with the first self-assembled protein or the second self-assembled protein.

According to the kit, the first self-assembled protein of the second self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the first fusion protein, the second fusion protein, the partner protein and the bait protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to kit, the light-induced heterodimerized protein or the partner protein may be homodimerized regardless of light irradiation. In this case, the light-induced heterodimerized protein or the partner protein capable of forming homodimer regardless of light irradiation may be CRY or PHR.

In an aspect of the present invention, a method for inhibiting a target protein reversibly using light-induced nanocluster formation, wherein the method comprises: expressing a fusion protein including self-assembled protein and a light-induced heterodimerzable protein, a partner protein forming a heterodimer with the light-induced heterodimerzable protein, and a target protein in a cell or a subject; and inducing light-induced formation of nanocluster by light having wavelength capable of forming the heterodimer between the light-induced heterodimerized protein and the partner protein, wherein the target protein is expressed as a fusion protein with the self-assembled protein or the partner protein.

According to the method, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the method, at least one protein among the fusion protein, and the partner protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the method, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may be homodimerized regardless of light irradiation. In this case, the light-induced heterodimerized protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter and a second polynucleotide encoding a second fusion protein comprising a partner protein capable of heterodimerizing with the light-induced heterodimerized protein, wherein the second polynucleotide is operably linked to the promoter; and optionally a third expression vector including a third gene construct containing a promoter and a third polynucleotide encoding a third fusion protein containing the target protein and the self-assembled protein, wherein the third polynucleotide is linked operably to the promoter, or the target protein is included in the second fusion protein.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, and the partner protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may be homodimerized regardless of light irradiation. In this case, the light-induced heterodimerized protein or the partner protein capable of forming homodimer regardless of light irradiation may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter and a second polynucleotide encoding a second fusion protein comprising a partner protein capable of heterodimerizing with the light-induced heterodimerized protein, wherein the second polynucleotide is operably linked to a promoter; and optionally a third expression vector including a third gene construct containing a promoter and a multicloning site for inserting a third polynucleotide encoding a bait protein interacting with the target protein, wherein the third polynucleotide is operably linked to the promoter, or the multicloning site is included within the second polynucleotide in order that the target protein is expressed as included in the second fusion protein.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, and the partner protein may contain a fluorescent protein in order to verify whether the protein nano-cluster is formed. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), far-red fluorescent protein or tetracysteine fluorescent motif.

According to the kit, the light-induced heterodimerized protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may be homodimerized regardless of light irradiation. In this case, the light-induced heterodimerized protein or the partner protein capable of forming homodimer regardless of light irradiation may be CRY or PHR.

Effect of the Invention

According to exemplary embodiments of the present invention, as described above, it is possible to analyze interaction between proteins and to control function of particular proteins reversibly and spatio-temproally by forming nanoclusters within a cell or a tissue efficiently. Of course, the scope of the present invention is not limited thereto.

BEST MODE

Definition of Terms

Figure 1:
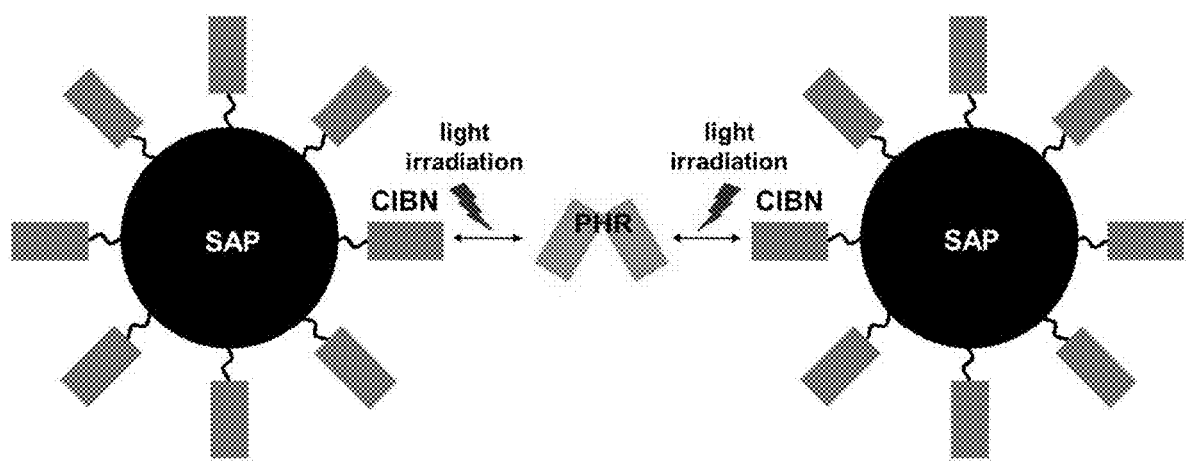
FIG. 1 is a schematic overview of the principles of nano-cluster formation induced by light irradiation.

The terms used in this document are designated as follows.

A "bait protein" used in this document means proteins that interact with target proteins.

A "target protein" used in this document means a partner protein interacting with the bait protein and may be referred as to a protein to be analyzed.

A "self-assembled protein" or "SAP" used in this document means a protein capable of forming an organized multimer without help of external mediators and representative self-assembled protein includes ferritin A "nano-cluster" or "protein nanocluster" used in this document refers to an agglometer colonized by the interaction between the nanoparticles formed by self-assembly of the self-assembled proteins.

A "light-induced heterodimerized protein" used in this document refers to a protein forming a heterodimer with other proteins when irradiated with light having a particular wavelength.

A "partner protein" used in this document refers to a target protein forming a heterodimer with the light-induced heterodimerized protein" when irradiated with light having a particular wavelength.

A "fusion protein" used in this document refers to a protein in which two or more proteins are connected each other by amino bond while maintaining the functionality of each unit protein.

A "heterodimer" used in this document means a dimer or a complex formed by two different proteins via the interaction between them.

A "homodimer" used in this document means a dimer or a complex formed by two same proteins via intermolecular interaction.

An "operably linked to" used in this document means that a particular polynucleotide can function when connected to other polynucleotides. In other words, "a polynucleotide encoding a particular protein, wherein the polynucleotide is operably linked to the promoter" means that the polynucleotide can be transcribed into mRNAs according to the action of the promoter and the mRNAs are translated to the protein and "a polyncleotide encoding a particular protein is operably linked to a polynucleotide encoding the other protein" means that the particular protein can be expressed as fused to the other protein.

A "CIB" used in this document means a cryptochrome-interacting basic-helix-loop-helix protein and a representative CIB is *Arabidopsis* CIB1 (GenBank No. NM_119618).

A "CIBN" used in this document means a N-terminal of the CIB, which is a part interacting with cryptochrome (CRY) when it is irradiated.

A "CRY" used in this document refers to a cryptochrome protein and a representative CRY is *Arabidopsis* CRY2 (GenBank No. NM_100320).

A "PHR" used in this document refers to an N-terminal of the CRY which is a phytolyase homologous region of CRY and interacts with the CIB or the CIBN when it is irradiated (Kennedy et al., *Nat. Methods,* 7(12): 973-975, 2010)

A "Phy" used in this document refers to a phytochrome protein and a representative Phy is *Arabidopsis* PhyA (GenBank No.: NM_001123784) and the Phy is known to interact with PIF (phytochrome interacting factor) (Min et al., *Nature,* 400: 781-784, 1999).

A "PIF" used in this document refers to a phytochrome interacting factor and a representative PIF includes *Arabidopsis* PIF1 (GenBank No.: NM_001202630), PIF3 (GenBank No.: NM_179295), PIF4 (GenBank No.: NM_180050), PIF5 (GenBank No.: NM_180690), PIF6 (GenBank No.: NM_001203231) and PIF7 (GenBank No.: NM_125520).

A "FKF" used in this document refers to a Flavin-binding, Kelch repeat, F-fox protein and a representative FKF is *Arabidopsis* FKF1 (GenBank No.: NM_105475). It is known to interact with GIGANTEA protein when it is irradiated (Sawa et al., *Science,* 318 (5848): 261-265, 2007).

A "GIGANTEA" used in this document refers to a protein related to phytochrome signal transduction and is known to regulate flowering time of flowers.

A "tetracysteine fluorescent" used in this document refers to a polypeptide containing an amino acid sequence of Cys-Cys-Xaa-Xaa-Cys-Cys (SEQ ID NO: 1), wherein the Xaa is any one amino acid except cysteine and fluorescent pattern varies depending on the type of Xaa and the length of the polypeptide (Adams et al., *J. Am. Chem. Soc.,* 124: 6063-6077, 2002).

Methods for analyzing protein interaction according to various embodiments of the present invention are described through the accompanying drawings.

FIG. 1 is a schematic overview of the principles of nano-cluster formation induced by light irradiation.

Figure 2:
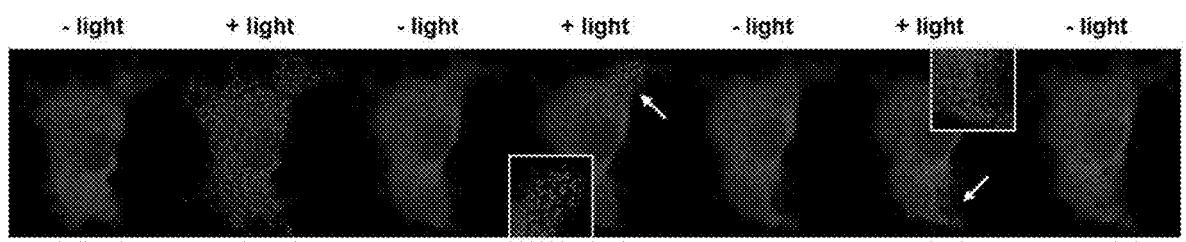
FIG. 2 is a fluorescence microscophic image showing an experimental result representing actual formation of nanocluster shown in FIG. 1.
Figure 3:
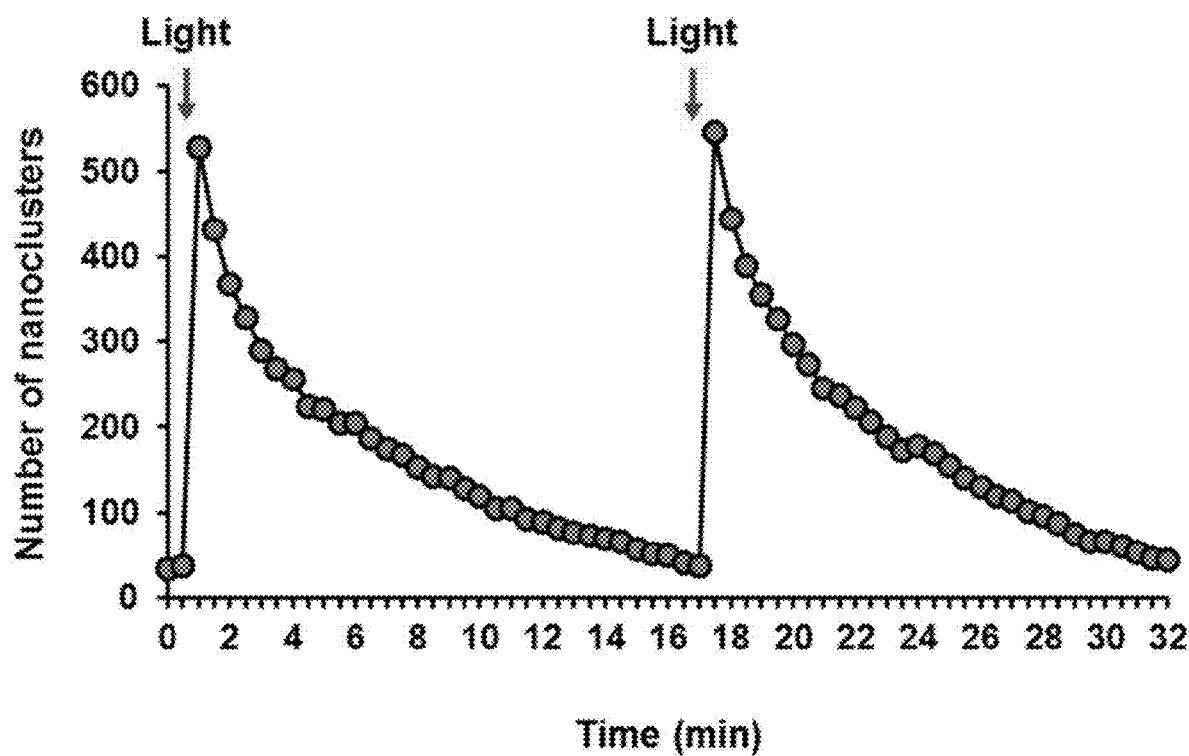
FIG. 3 is a graph showing the induced nano-cluster formation and dissociation process over a period of time.

The present inventors hypothesized that a protein nano-cluster may be formed by light-induced interaction between two light-induced heterodimerized proteins, if a light-induced heterodimerized protein expressed as fused to a self-assembled protein such as ferritin and a partner protein interacting with the light-induced heterodimerized protein by light irradiating are co-expressed and irradiated with a light having a particular wavelength capable of inducing the light-induced interaction between two proteins (See FIG. 1). Thus, the present inventors co-transfected the cell with an expression vector containing a gene construct encoding a fusion protein ferritin which is a self-assembled protein, CIBN which is a light-induced heterodimerized protein, and a fluorescent protein and an expression vector containing a gene construct encoding PHR which is a partner protein and irradiated the co-transfected cell with a light having wavelength inducing the interaction between the CIBN and the PHR observed sopts emitting strong fluorescent within a cell in order to verify the hypothesis, and then the present inventors observed sopts emitting strong fluorescent within a cell (FIG. 2) and confirmed that waxes and wanes of number of spots coincided with light irradiation cycle (FIG. 3). This result proves that a nano-cluster between self-assembled fusion proteins within a cell was formed by light irradiation.

In an aspect to the present invention, an expression vector comprising a polynucleotide encoding a fusion protein comprising a light-induced heterodimerzable protein, and a self-assembled protein is provided.

According to the expression vector, the light-induced heterodimerized protein may be CIB, CIBN PhyB, PIF FKF1, GIGANTEA, CRY, or PHR.

According to the expression vector, the self-assembled protein may be ferritin, virus capsid protein, ferritin-like protein, calcium/calmodulin-dependent protein kinase II alpha subunit (CaMKIIα) or DsRed, and the virus capsid protein may be a capsid protein derived from CCMV (cowpea chlorotic mottle virus), Norwalk virus, SV40, or HPV (human papilloma virus). The description of the self-assembled protein, will be applied to a first self-assembled protein and a second self-assembled protein in the same manner which are described later.

According to the expression vector, the fusion protein may further contain a fluorescent protein, and the fluorescent protein may be added to N-terminal or C-terminal of the fusion protein and may be inserted between the light-induced heterodimerized protein and the self-assembled protein. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP (enhanced green fluorescent protein), Emerald (Tsien, *Annu. Rev. Biochem.*, 67: 509-544, 1998), Superfolder (Pedelacq et al., *Nat. Biotech.*, 24: 79-88, 2006), GFP (Prendergast et al., *Biochem.*, 17 (17): 3448-3453, 1978), Azami Green (Karasawa, et al., *J. Biol. Chem.*, 278: 34167-34171, 2003), TagGFP (Evrogen, Russia), TurboGFP (Shagin et al., *Mol. Biol. Evol.*, 21 (5): 841-850, 2004), ZsGreen (Matz et al., *Nat. Biotechnol.*, 17: 969-973, 1999) or T-Sapphire (Zapata-Hommer et al, *BMC Biotechnol.*, 3:5, 2003). The yellow fluorescent protein may be EYFP (enhanced yellow fluorescent protein, Tsien, *Annu. Rev. Biochem.*, 67: 509-544, 1998), Topaz (Hat et al., *Ann. NY Acad. Sci.*, 1: 627-633, 2002), Venus (Nagai et al., *Nat. Biotechnol.*, 20(1): 87-90, 2002), mCitrine (Griesbeck et al., *J. Biol. Chem.*, 276: 29188-29194, 2001), Ypet (Nguyet and Daugherty, *Nat. Biotechnol.*, 23(3): 355-360, 2005), TagYFP (Evrogen, Russia), PhiYFP (Shagin et al., *Mol. Biol. Evol.*, 21(5): 841-850, 2004), ZsYellow1 (Matz et al., *Nat. Biotechnol.*, 17: 969-973, 1999), or mBanana (Shaner et al., *Nat. Biotechnol.*, 22: 1567-1572, 2004). The red fluorescent protein may be mRuby (Kredel et al., *PLoS ONE*, 4(2): e4391, 2009), mApple (Shaner et al., *Nat. Methods*, 5(6): 545-551, 2008), mStrawberry (Shaner et al., *Nat. Biotechnol.*, 22: 1567-1572, 2004) and AsRed2 (Shanner et al., *Nat. Biotechnol.*, 22: 1567-1572, 2004) or mRFP (Campbell et al., *Proc. Natl. Acad. Sci. USA,* 99(12): 7877-7882, 2002). The orange fluorescent protein may be Kusabira Orange (Karawawa et al., *Biochem. J.* 381(Pt 1): 307-312, 2004), Kusabira Orange2 (MBL International Corp., Japan), mOrange (Shaner et al., *Nat. Biotechnol.*, 22: 1567-1572, 2004), mOrange2 (Shaner et al., *Nat. Biotechnol.*, 22: 1567-1572, 2004), dTomato (Shaner et al., *Nat. Biotechnol.*, 22: 1567-1572, 2004), dTomato-Tandem (Shaner et al., *Nat. Biotechnol.*, 22: 1567-1572, 2004), TagRFP (Merzlyak et al., *Nat. Methods*, 4(7): 555-557, 2007), TagRFP-T (Shaner et al., *Nat. Methods*, 5(6): 545-551, 2008), DsRed (Baird et al., *Proc. Natl. Acad. Sci. USA,* 97: 11984-11989, 1999), DsRed2 (Clontech, USA), DsRed-Express (Clontech, USA), DsRed-Monomer (Clontech, USA), or mTangerine (Shaner et al., *Nat Biotechnol,* 22: 1567-1572, 2004 above). The cyan fluorescent protein may be ECFP (enhanced cyan fluorescent protein, Cubitt et al., *Trends Biochem. Sci.*, 20: 448-455, 1995), mECFP (Ai et al., *Biochem. J.,* 400(3): 531-540, 2006), mCerulean (Koushik et al., *Biophys. J.,* 91(12): L99-L101, 2006), CyPet (Nguyet and Daugherty, *Nat. Biotechnol.*, 23 (3): 355-360, 2005), AmCyan1 (Matz et al., *Nat. Biotechnol.,* 17: 969-973, 1999), Midori-Ishi Cyan (Karawawa et al., *Biochem. J.,* 381(Pt 1): 307-312, 2004), TagCFP (Evrogen, Russia) or mTFP1, (Ai et al, *Biochem. J.,* 400 (3): 531-540, 2006). The blue fluorescent protein may be EBFP (enhanced blue fluorescent protein, Clontech, USA), EBFP2 (Ai et al., *Biochemistry,* 46 (20): 5904-5910. 2007), Azurite (Mena et al., *Nat. Biotechnol.*, 24: 1569-1571, 2006) or mTagBFP (Subach et al., *Chem. Biol.,* 15(10): 1116-1124, 2008). The far red fluorescent protein may be mPlum (Wang et al., *Proc. Natl. Acad. Sci. USA,* 101: 16745-16749, 2004), mCherry (Shanner et al., *Nat. Biotechnol.,* 22: 1567-1572, 2004), dKeima-Tandem (Kogure et al., *Methods,* 45(3): 223-226, 2008), JRed (Shagin et al., *Mol. Biol. Evol.,* 21(5): 841-850, 2004), mRaspberry (Shanner et al., *Nat. Biotechnol.,* 22: 1567-1572, 2004), HcRed1 (Fradkov et al., *Biochem. J.,* 368(Pt 1): 17-21, 2002), HcRed-Tandem (Fradkov et al., *Nat. Biotechnol.,* 22(3): 289-296, 2004), AQ143 (Shkrob et al., *Biochem. J.,* 392: 649-654, 2005). The tetracysteine fluorescent motif may be a polypeptide including an amino acid sequence of Cys-Cys-Xaa-Xaa-Cys-Cys (SEQ ID NO: 1), wherein the Xaa is any one amino acid except cysteine. The description for the fluorescent proteins applied to a first fluorescent protein, a second fluorescent proteins, a third fluorescent protein and a fourth fluorescent protein which will be described later in a same manner.

In an aspect to the present invention, a kit for forming light-induced protein nano-clusters comprising a first expression vector including a polynucleotide encoding a first fusion protein comprising a light-induced heterodimerized protein and a first self-assembled protein; and a second expression vector including a polynucleotide encoding a partner protein capable of forming a heterodimer with the light-induced heterodimerizing protein, or a second fusion protein containing the partner protein and a second self-assembled protein is provided.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerzed protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerzed protein is GIGANTEA. The PIF may be PIF3 or PIF6. Among the light-induced heterodimerized protein or the partner protein, CRY or PHR may be homodimerized regardless of light irradiation.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the kit, at least one among the first fusion protein, the partner protein and the second fusion protein may further comprises a fluorescent protein and the fluorescent protein may be added to N-termius or C-terminus of the first fusion protein, the partner protein and/or the second fusion protein or may be inserted between the light-induced heterodimerized protein and the first self-assembled protein or between the partner protein and the second self-assembled protein. At this time, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

In another aspect to the present invention, a method for forming a protein nano-cluster is provided, wherein the method comprises: providing a first expression vector including a polynucleotide encoding a first fusion protein comprising a light-induced heterodimerized protein and a first self-assembled protein; and a second expression vector including a polynucleotide encoding a partner protein capable of forming a heterodimer with the light-induced heterodimerizing protein, or a second fusion protein containing the partner protein and a second self-assembled protein;

transforming a cell, a tissue or a subject with the first expression vector and the second expression vector; and irradiating light having wavelength capable of indcucing heterodimerization between the light-induced heterodimerized protein and the partner protein to the cell, the tissue or the subject.

According to the method, the light-induced heterodimerized protein may be CIB, CIBN, PhyB, PIF, FKF1, GIGANTEA, CRY, or PHR.

According to the method, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the method, at least one among the first fusion protein, the partner protein and the second fusion protein may further comprises a fluorescent protein and the fluorescent protein may be added to N-termius or C-terminus of the first fusion protein, the partner protein and/or the second fusion protein or may be inserted between the light-induced heterodimerized protein and the first self-assembled protein or between the partner protein and the second self-assembled protein. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

The method and kit for forming a protein nano-cluster according to an embodiment of the present invention may be useful for screening a substance regulating protein-protein interaction as well as analyzing protein-protein interaction by inducing the formation of a nano-cluster between nano-particles formed by protein self-assembly by light irradiation. In addition, the method and kit for forming a protein nano-cluster according to an embodiment of the present invention may be useful for analyzing real-time protein-protein interaction within living cells with minimal cell damage, because it can induce protein-protein interaction reversibly. Moreover, the method and kit for forming a protein nano-cluster according to an embodiment of the present invention may be useful for inhibiting a target protein reversibly by entrapping the target protein using a bait protein interacting the target protein.

Figure 4:
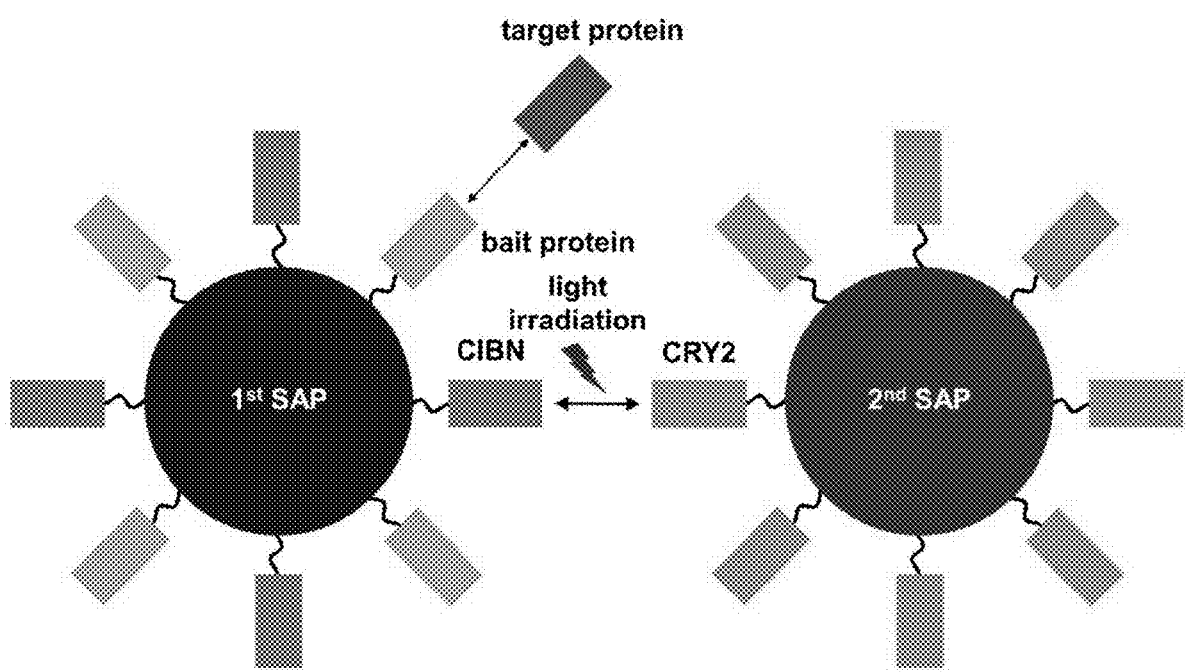
FIG. 4 is a schematic overview representing the principles of a method for analyzing the interaction between the proteins using the nanocluster formation according to an embodiment of the present invention.

The aforementioned method for analyzing protein-protein interaction and the method for inhibiting a target protein reversibly are described in detail as follows:

In an aspect of the present invention, a kit for analyzing interaction between proteins is provided, wherein the kit comprises: a first expression vector including a first gene construct containing a promoter and a first polynucleotide encoding a first fusion protein comprising a bait protein and a first self-assembled protein, wherein the first polynucleotide is operably linked to the promoter: a second expression vector including a second gene construct containing a promoter and a second polynucleotide encoding a second fusion protein comprising a light-induced heterodimerized protein and the first self-assembled protein, wherein the second polynucleotide is operably linked to the promoter; a third expression vector including a third gene construct containing a promoter and a third polynucleotide encoding a third fusion protein comprising a partner protein interacting with the light-induced heterodimerized protein, a second fluorescent protein, and a second self-assembled protein, wherein the third polynucleotide is operably linked to the promoter; and a fourth expression vector including a fourth gene construct containing a promoter and a fourth polynucleotide encoding a fourth fusion protein comprising a target protein and a third fluorescent protein, wherein the fourth polynucleotide is operably linked to the promoter, with the proviso that at least one fusion protein among the first fusion protein and the second fusion protein contains a first fluorescent protein, wherein the first self-assembled protein and the second self-assembled protein do not interact each other, and wherein all the fluorescent proteins emit different wavelengths of light, wherein the first self-assembled protein or the second self-assembled protein may be omitted from any fusion proteins containing DsRed when either the first fluorescent protein or the second fluorescent protein is DsRed. (FIG. 4).

According to the kit, the order of the bait protein, the first self-assembled protein and optionally the first fluorescent protein within the first fusion protein may be rearranged. For example, the first fusion protein may consist of the bait protein, the first fluorescent protein and the first assemblem protein in consecutive order or may consist of the first self-assembled protein and the first fluorescent protein and the bait protein in consecutive order. Similarly, the order of the light-induced heterodimerized protein, the first self-assembled protein and the optional first fluorescent protein within the second fusion protein may be rearranged as necessary. For example, the second fusion protein may consist of the light-induced heterodimerized protein, the first fluorescent protein and the first self-assembled protein in consecutive order or may consist of the first self-assembled protein, the first fluorescent protein and the light-induced heterodimerized protein in consecutive order. Similarly, the order of the partner protein, the second fluorescent protein and the second self-assembled protein within the third fusion protein may be adjusted as necessary. For example, the third fusion protein may consist of the partner protein, the second fluorescent protein and the second self-assembled protein in consecutive order or may consist of the second self-assembled protein and the partner protein, in consecutive order. Finally, in the fourth fusion protein, the target protein may be positioned at N-terminal or the third fluorescent protein may be positioned at the N-terminal.

The all fusion proteins described above may contain at least one linker between the unit proteins consisting each fusion protein.

In another aspect of the present invention, a kit for analyzing interaction between proteins is provided, wherein the kit comprises: a first expression vector including a first gene construct containing a promoter, a first polynucleotide encoding a first fusion protein comprising a first self-assembled protein and a multicloning site in which a polynucleotide encoding a bait protein is operably linked to the first polynucleotide and wherein the first polynucleotide is operably linked to the promoter; a second expression vector including a second gene construct containing a promoter, and a second polynucleotide encoding a second fusion protein comprising a light-induced heterodimerized protein, wherein the second polynucleotide is operably linked to the promoter; a third expression vector including a third gene construct containing a promoter and a third polynucleotide encoding a third fusion protein comprising a partner protein interacting with the light-induced heterodimerized protein, a second fluorescent protein, and a second self-assembled protein, wherein the third polynucleotide is operably linked to the promoter; and a fourth expression vector including a fourth gene construct containing a promoter and a fourth polynucleotide encoding a fourth fusion protein comprising a third fluorescent protein and a multicloning site in which a polynucleotide encoding a target protein is operably linked to the fourth polynucleotide and wherein the fourth polynucleotide is operably linked to the promoter, with the proviso that at least one fusion protein among the first fusion protein and the second fusion protein contains a first fluorescent protein, wherein the first self-assembled protein and the second self-assembled protein do not interact each other, and wherein all the fluorescent proteins emit different wavelengths of light, wherein the first self-assembled protein or the second self-assembled protein may be omitted from any fusion proteins containing DsRed when either the first fluorescent protein or the second fluorescent protein is DsRed.

According to the kit, the first to third fluorescent proteins may be green fluorescent protein (GFP), yellow fluorescent protein (YFP), red fluorescent protein (RFP), orange fluorescent protein, cyan fluorescent protein (CFP), blue fluorescent protein (BFP), TagCFP, DsRed or tetracysteine fluorescent motif, independently.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6. Among the light-induced heterodimerized protein or the partner protein, CRY or PHR may be homodimerized regardless of light irradiation.

According to the kit, the promoter may be a eukaryotic promoter.

FIG. 4. is a schematic overview representing the principles of a method for analyzing the interaction between the proteins using the nanocluster formation according to an embodiment of the present invention. As shown in FIG. 4, the light-induced nano-cluster may be formed by the light-induced interaction between a first nanoparticle including a light-induced heterodimerized protein (i.e., CIBN) and a second nanoparticle including a partner protein interacting with the light-induced heterodimerized protein (i.e., PHR).

In this case, the first nanoparticle is formed by self-assembly of two fusion protein (a first fusion protein and a second fusion protein) expressed by two gene construct, respectively and the first fusion protein and the second fusion protein have a common self-assembled protein (the first self-assembled protein, $1^{st}$ SAP), thus a hetero-assembled nanoparticle is formed. In order to check the expression of the fusion proteins and the formation of the nanocluster, the first fusion protein and/or the second fusion protein contain a fluorescent protein. On the other hand, the second nanoparticle is a homo-assembled nanoparticle formed by self assembly of a third fusion protein comprising a second self-assembled protein ($2^{nd}$ SAP) not interacting with the first self-assembled protein and a partner protein interacting with the light-induced heterodimerized protein by light irradiation. The third fusion protein contains a second fluorescent protein emitting different wavelengths of light to the first fluorescent protein in order to check the expression of the fusion protein and the formation of nanoclusters. On the other hand, the target protein to be examined whether it interacts with the bait protein is expressed as a fusion protein with a third fluorescent protein emitting different wavelengths of light to the first and second fluorescent protein. If the target protein interacts with the bait protein, the nano-cluster formed by the light-induced interaction between the light-induced heterodimerized protein and the partner protein and the target protein will be co-localized. However, if the target protein does not interact with the bait protein, fluorescent corresponding the target protein will be dispersed throughout cytoplasm of a cell rather than forming strong fluorescent spots which are formed by the first nanopartides and the second nanoparticles. On the other hand, nano-clusters formed by the homo-interaction between the first nanoparticles are distinguished from the nano-clusters formed by the hetero-interaction, since the fluorescent pattern formed by the first nanoparticles does not correspond to that formed by the second nanoparticles.

The CIBN illustrated in FIG. 4 refers to an N-terminal fragment (1-170 a.a.) of *A. thaliana* bHLH63 protein. It is a representative light-induced heterodimerized protein known to interact with PHR (phytolyase homologous region) which is an N-terminal fragment (1-488 a.a.) of *A. thaliana* cryptochrome 2 when it is irradiated with blue light having 488 nm of wavelength (Liu et al., *Science,* 322(5907): 1535-1539, 2009). Hereinafter, the light-induced heterodimerized protein will be designated as CIBN and the partner protein will be referred to CRY2 or PHR, for convenience. The light-induced heterodimerized protein may be PhyB, PIF3, PIF6, FKF1, or GIGANTEA, etc. besides CIB and CIBN. The PhyB is *A. thaliana* phytochrome B protein and known to interact with PIF (phytochrome-interacting factor) when irradiated with red light (Castillon et al., *Trends Plant Sci.,* 12(11): 514-521, 2007). FKF1 (flavin-binding, kelch repat, F-box 1) is a protein regulated by time which is known to regulate flowering time and interacts with GIGANTEA when irradiated with blue light (Sawa et al., *Science,* 318 (5848): 261-265, 2007). GIGANTEA is a nuclear protein involved in phytochrome signal transduction in *A. thaliana* (Huq et al., *Proc. Natl. Acad. Soc. USA,* 97(17): 9789-9794, 2000).

Figure 5:
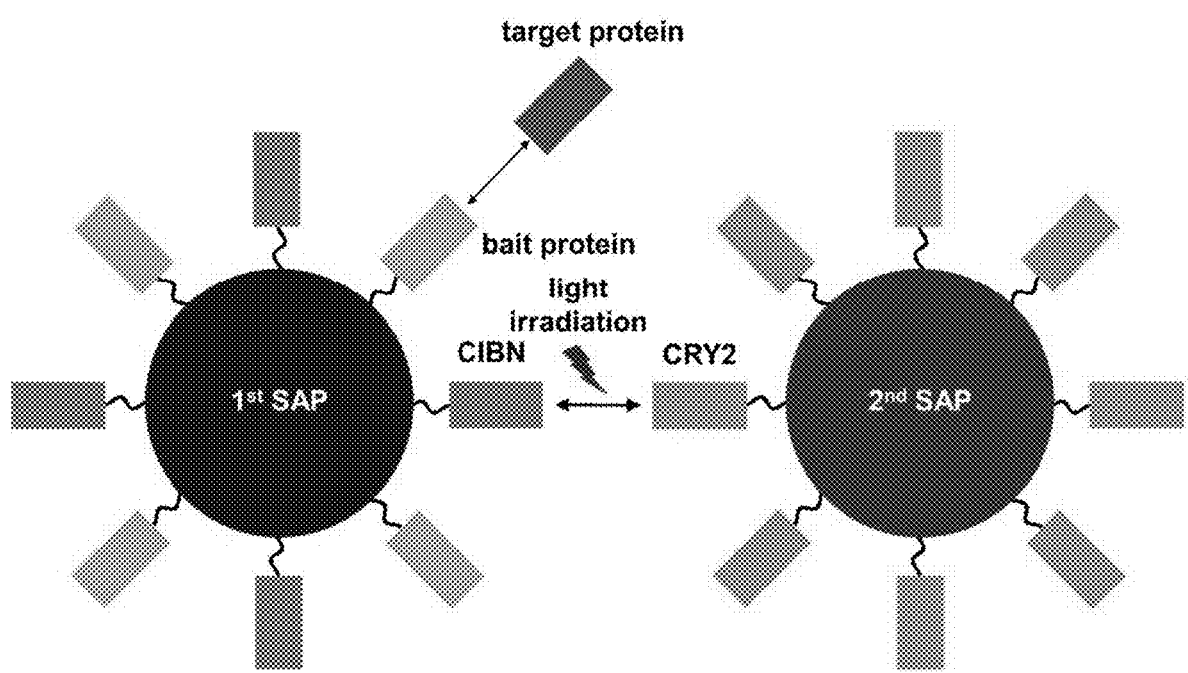
FIG. 5 is a schematic overview representing the principles of a method for analyzing the interaction between the proteins using the nanocluster formation according to another embodiment of the present invention.

In another aspect of the present invention, a kit for analyzing interaction between proteins is provided, wherein the kit comprises: a first expression vector including a first gene construct containing a promoter and a first polynucleotide encoding a first fusion protein comprising a light-induced heterodimerized protein, a first fluorescent protein and a first self-assembled protein, wherein the first polynucleotide is operably linked to the promoter; a second expression vector including a second gene construct containing a promoter and a second polynucleotide encoding a second fusion protein comprising a partner protein interacting with the light-induced heterodimerized protein, a second fluorescent protein and a bait protein, wherein the second polynucleotide is operably linked to the promoter; and a third expression vector including a third gene construct containing a promoter and polynucleotide encoding a third fusion protein comprising a target protein, a third fluorescent protein and a second self-assembled protein, wherein the third polynucleotide is operably linked to the promoter, with the proviso that all the fluorescent proteins emit different wavelengths of light, wherein the first self-assembled protein and the second self-assembled protein do not interact each other, and wherein the first self-assembled protein or the second self-assembled protein may be omitted from any fusion proteins containing DsRed when either the first fluorescent protein or the third fluorescent protein is DsRed (FIG. 5).

In another aspect of the present invention, a kit for analyzing interaction between proteins is provided, wherein the kit comprises: a first expression vector including a first gene construct containing a promoter and a first polynucleotide encoding a first fusion protein comprising a light-induced heterodimerized protein, a first fluorescent protein and a first self-assembled protein, wherein the first polynucleotide is operably linked to the promoter; a second expression vector including a second gene construct containing a promoter and a second polynucleotide encoding a second fusion protein comprising a partner protein interacting with the light-induced heterodimerized protein and a second fluorescent protein and a multicloning site in which a polynucleotide encoding a bait protein is operably linked to the second polynucleotide, wherein the second polynucleotide is operably linked to the promoter; and a third expression vector including a third gene construct containing a promoter and a third polynucleotide encoding a third fusion protein comprising a third fluorescent protein and a second self-assembled protein and a multicloning site in which a polynucleotide encoding a target protein is operably linked to the third polynucleotide, wherein the third polynucleotide is operably linked to the promoter, with the proviso that all the fluorescent proteins emit different wavelengths of light, wherein the first self-assembled protein and the second self-assembled protein do not interact each other, and wherein the first self-assembled protein or the second self-assembled protein may be omitted from any fusion proteins containing DsRed when either the first fluorescent protein or the third fluorescent protein is DsRed.

According to the kit, the first to third fluorescent proteins may be green fluorescent protein (GFP), yellow fluorescent protein (YFP), red fluorescent protein (RFP), orange fluorescent protein, cyan fluorescent protein (CFP), blue fluorescent protein (BFP), TagCFP, DsRed or tetracysteine fluorescent motif, independently.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). However, the first self-assembled protein and the second self-assembling protein may be same or different when they are used at the same time.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the promoter may be a eukaryotic promoter.

FIG. 5 is a schematic overview representing the principles of a method for analyzing the interaction between the proteins using the nanocluster formation according to another embodiment of the present invention. As shown in FIG. 5, nano-clusters are not generated directly by the interaction between nanoparticles formed by self-assembly rather formed indirectly by a cluster formation linker. Particularly, a first nanoparticle is generated by self-assembly of the first fusion protein containing the light-induced heterodimerized protein, the first fluorescent protein and the first self-assembled protein ($1^{st}$ SAP). A second nanoparticle is formed by self-assembly of the third fusion protein containing the target protein and the third fluorescent protein emitting different wavelengths of light to the first fluorescent protein and the second self-assembled protein. When a second fusion protein containing the partner protein besides the first nanoparticle and the second nanoparticle, the second fluorescent protein and the bait protein is co-expressed within a cell, a heterodimer is formed between the light-induced heterodimerized protein and the partner protein and if the target protein displayed onto the surface of the second nanoparticle interacts with the bait protein a nanocluster is generated by the linkage of the second fusion protein and it is possible to determine whether a nano-cluster is generated and it is false-positive or false-negative through unique fluorescent patterns of each fusion protein. If the target protein does not interact with the bait protein, no nano-cluster is generated. On the contrary, if nano-clusters are formed by homodimerization of any one among the light-induced heterodimerized protein, the partner protein, the bait protein and the target protein, one can distinguish false-positive and false-negative through different fluorescent patterns according to each fluorescent protein.

Figure 6:
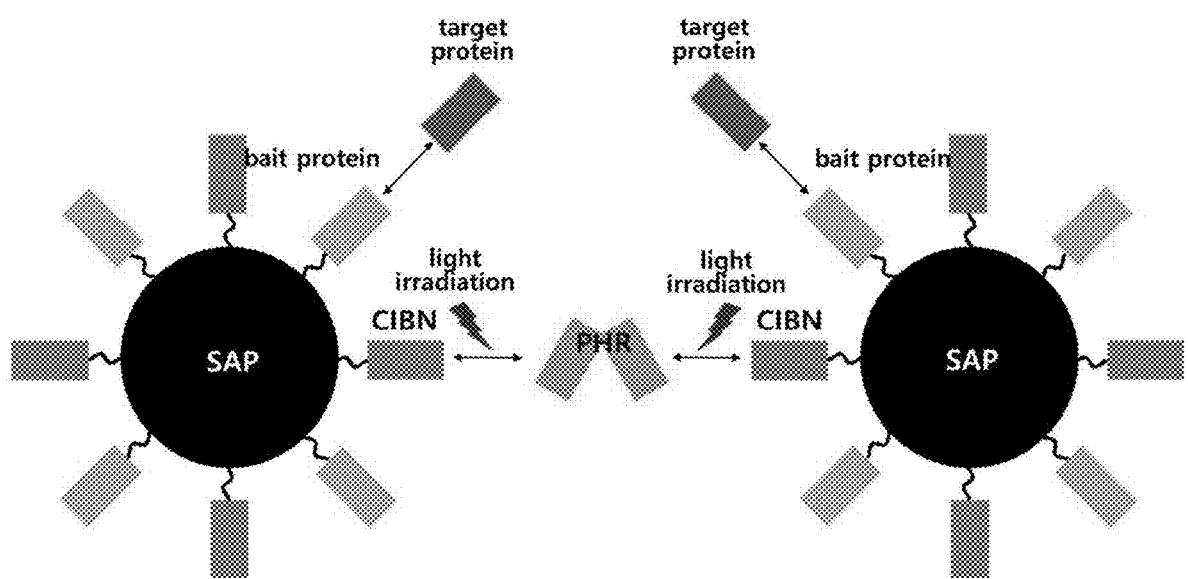
FIG. 6 is a schematic overview representing the principles of a method for analyzing the interaction between the proteins using the nanocluster formation according to still another embodiment of the present invention.

In another aspect of the present invention, a kit for analyzing interaction between proteins is provided, wherein the kit comprises: a first expression vector including a first gene construct containing a promoter, a first polynucleotide encoding a first fusion protein comprising a bait protein and a self-assembled protein, wherein the first polynucleotide is operably linked to the promoter; a second expression vector including a second gene construct containing a promoter, and a second polynucleotide encoding a second fusion protein comprising a light-induced heterodimerized protein and the self assembled protein, wherein the second polynucleotide is operably linked to the promoter; a third expression vector including a third gene construct containing a promoter and a third polynucleotide encoding a third fusion protein comprising at least two repeated partner proteins interacting with the light-induced heterodimerized protein, a second fluorescent protein, wherein the third polynucleotide is operably linked to the promoter; and a fourth expression vector including a fourth gene construct containing a promoter and a fourth polynucleotide encoding a fourth fusion protein comprising a third fluorescent protein wherein the fourth polynucleotide is operably linked to the promoter, with the proviso that at least one fusion protein among the first fusion protein and the second fusion protein contains a first fluorescent protein, wherein all fluorescent proteins emit different wavelengths of light and wherein the first self-assembled protein or the second self-assembled protein may be omitted from the first fusion protein or the second fusion protein when the first fluorescent protein protein is DsRed (FIG. 6).

In another aspect of the present invention, a kit for analyzing interaction between proteins is provided, wherein the kit comprises: a first expression vector including a first gene construct containing a promoter, a first polynucleotide encoding a first fusion protein containing self-assembled protein and a multicloning site in which a polynucleotide encoding a bait protein is operably linked to the first polynucleotide and wherein the first polynucleotide is operably linked to the promoter; a second expression vector including a second gene construct containing a promoter, and a second polynucleotide encoding a second fusion protein comprising a light-induced heterodimerized protein and the self assembled protein, wherein the second polynucleotide is operably linked to the promoter; a third expression vector including a third gene construct containing a promoter and a third polynucleotide encoding a third fusion protein comprising at least two repeated partner proteins interacting with the light-induced heterodimerized protein, a second fluorescent protein, wherein the third polynucleotide is operably linked to the promoter; and a fourth expression vector including a fourth gene construct containing a promoter and a fourth polynucleotide encoding a fourth fusion protein comprising a third fluorescent protein wherein the fourth polynucleotide is operably linked to the promoter, with the proviso that at least one fusion protein among the first fusion protein and the second fusion protein contains a first fluorescent protein, wherein all the fluorescent proteins emit different wavelengths of light, and wherein the first self-assembled protein or the second self-assembled protein may be omitted from the first fusion protein or the second fusion protein when the first fluorescent protein is DsRed.

According to the kit, the first to third fluorescent proteins may be green fluorescent protein (GFP), yellow fluorescent protein (YFP), red fluorescent protein (RFP), orange fluorescent protein, cyan fluorescent protein (CFP), blue fluorescent protein (BFP), TagCFP, DsRed or tetracysteine fluorescent motif, independently.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, the promoter may be a eukaryotic promoter.

FIG. 6 is a schematic overview representing the principles of a method for analyzing the interaction between the proteins using the nanocluster formation according to still another embodiment of the present invention. As shown in FIG. 6, according to the example, a single nanoparticle is used. The nanoparticle forms a hetero-assembled nanoparticle between a first fusion protein comprising a light-induced heterodimerized protein and a self-assembled protein, and a second fusion protein comprising a bait protein and the self-assemble protein. In this case, the first fluorescent protein is incorporated to either the first fusion protein or the second fusion protein in order to determine whether the fusion proteins are expressed and nano-clusters are generated. The formation of nano-clusters is accomplished by the light-induced interaction between the partner protein incorporated in the third fusion protein and the light-induced heterodimerized protein. The third fusion protein may comprise at least two repeated the partner proteins. Alternately a single copy of the partner protein may be used for the nano-cluster formation when the partner protein can be homodimerized like PHR. The interaction between the bait protein and the target protein may be analyzed by determining whether the fourth fusion protein containing the target protein the third fluorescent protein interacts with the nanoparticles, wherein the fourth fusion protein is expressed independent of the first to third fusion protein. In this case, nano-clusters are generated all the time by light irradiation and if there is an interaction between the bait protein and the target protein, the fluorescent pattern generated by the fourth fusion protein will be same with that generated by the nano-cluster formation. On the contrary, if there is no interaction between the bait protein and the target protein the fluorescent pattern generated by the fourth fusion protein will be a dispersed one unlike that generated by the nano-cluster formation.

Figure 7:
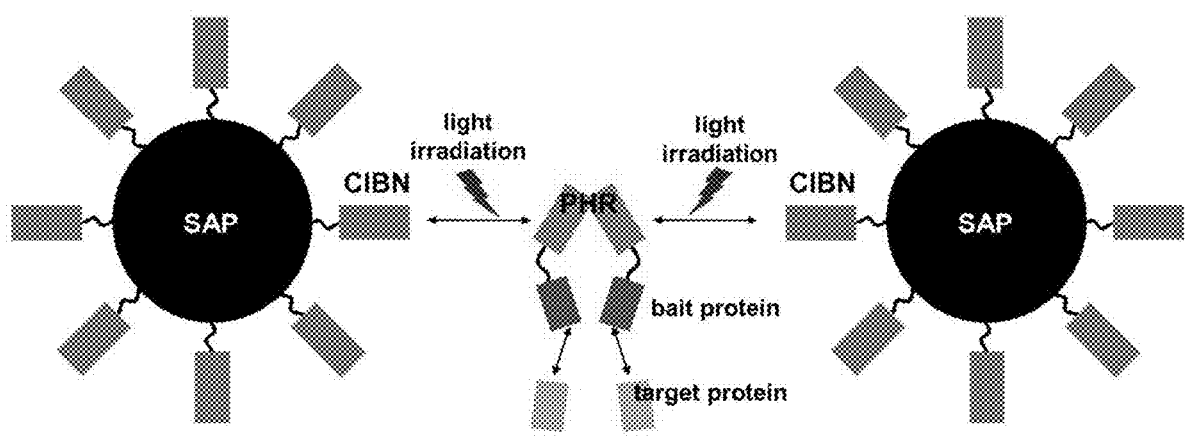
FIG. 7 is a schematic overview representing the principles of a method for analyzing the interaction between the proteins using the nanocluster formation according to still another embodiment of the present invention.

In another aspect of the present invention, a kit for analyzing interaction between proteins is provided, wherein the kit comprises: a first expression vector including a first gene construct containing a promoter, a first polynucleotide encoding a first fusion protein comprising a light-induced heterodimerized protein, a first fluorescent protein and a self-assembled protein, wherein the first polynucleotide is operably linked to the promoter; a second expression vector including a second gene construct containing a promoter, and a second polynucleotide encoding a second fusion protein comprising a partner protein interacting with the light-induced heterodimerized protein and forming a homodimer by itself, a second fluorescent protein and a bait protein, wherein the second polynucleotide is operably linked to the promoter; and a third expression vector including a third gene construct containing a promoter and a third polynucleotide encoding a third fusion protein comprising a target protein and a third fluorescent protein, wherein the third polynucleotide is operably linked to the promoter; with the proviso that all the fluorescent proteins emit different wavelengths of light and the self-assembled protein may be omitted from the first fusion protein when the first fluorescent protein is DsRed (FIG. 7).

In another aspect of the present invention, a kit for analyzing interaction between proteins is provided, wherein the kit comprises: a first expression vector including a first gene construct containing a promoter, a first polynucleotide encoding a first fusion protein comprising a light-induced heterodimerized protein, a first fluorescent protein and a self-assembled protein, wherein the first polynucleotide is operably linked to the promoter; a second expression vector including a second gene construct containing a promoter, and a second polynucleotide encoding a second fusion protein comprising a partner protein interacting with the light-induced heterodimerized protein and forming a homodimer by itself, and a second fluorescent protein and a multicloning site in which a polynucleotide encoding a bait protein is operably linked to the second polynucleotide, wherein the second polynucleotide is operably linked to the promoter; and a third expression vector including a third gene construct containing a promoter and a third polynucleotide encoding a third fusion protein comprising a third fluorescent protein, and a multicloning site in which a polynucleotide encoding a target protein is operably linked to the third polynucleotide, wherein the third polynucleotide is operably linked to the promoter; with the proviso that all the fluorescent proteins emit different wavelengths of light and the self-assembled protein may be omitted from the first fusion protein or the second fusion protein when the first fluorescent protein is DsRed.

According to the kit, the light-induced heterodimerized protein may be CIB, or CIBN.

According to the kit, the partner protein is a protein capable of forming a heterodimer with the light-induced protein by light irradiation and forming a homodimer regardless of light irradiation and may be CRY or PHR.

According to the kit, the first to third fluorescent proteins may be green fluorescent protein (GFP), yellow fluorescent protein (YFP), red fluorescent protein (RFP), orange fluorescent protein, cyan fluorescent protein (CFP), blue fluorescent protein (BFP), TagCFP, DsRed or tetracysteine fluorescent motif, independently.

According to the kit, the self-assembled may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, the promoter may be a eukaryotic promoter.

FIG. 7 is a schematic overview representing the principles of a method for analyzing the interaction between the proteins using the nanocluster formation according to still another embodiment of the present invention. As shown in FIG. 7, according to the example, a single nanoparticle is used. The nanoparticle is generated by self-assembly of the first fusion protein containing forms a hetero-assembled nanoparticle between the first fusion protein comprising a light-induced heterodimerized protein, the first fluorescent protein and the self-assembled protein, and the second fusion protein containing the partner protein, the second fluorescent protein and the bait protein and the self-assemble protein. In this case, the first fluorescent protein is incorporated to either the first fusion protein or the second fusion protein in order to determine whether the fusion proteins are expressed and nano-clusters are generated. The formation of nano-clusters is accomplished by the light-induced interaction between the partner protein incorporated in the third fusion protein and the light-induced heterodimerized protein. The third fusion protein may comprise at least two repeated the partner proteins. Alternately a single copy of the partner protein may be used for the nano-cluster formation when the partner protein can be homodimerized like PHR. The interaction between the bait protein and the target protein may be analyzed by determining whether the fourth fusion protein containing the target protein the third fluorescent protein interacts with the nanoparticles, wherein the fourth fusion protein is expressed independent of the first to third fusion protein. In this case, nano-clusters are generated all the time by light irradiation and if there is an interaction between the bait protein and the target protein, the fluorescent pattern generated by the fourth fusion protein will be same with that generated by the nano-cluster formation. On the contrary, if there is no interaction between the bait protein and the target protein, the fluorescent pattern generated by the fourth fusion protein will be a dispersed one unlike that generated by the nano-cluster formation.

Figure 8:
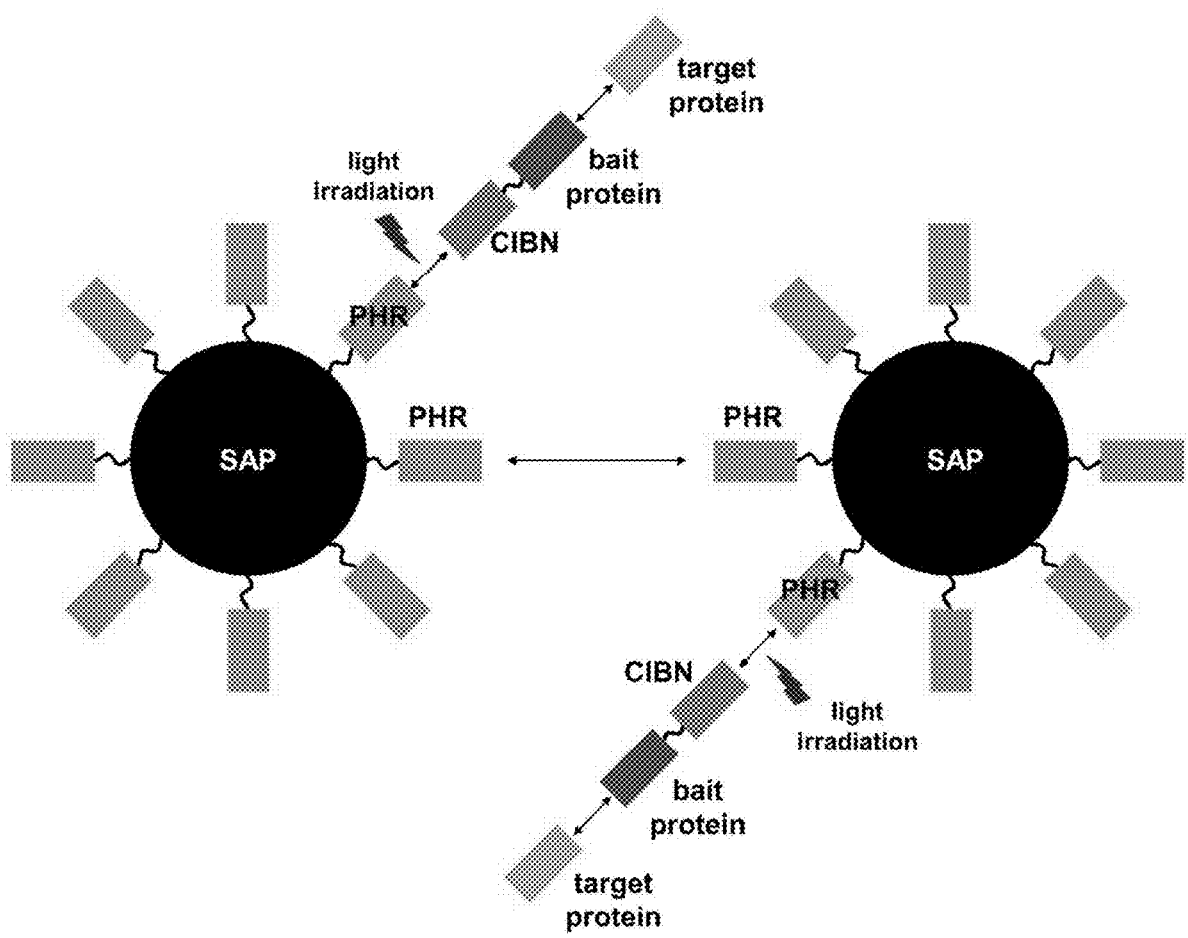
FIG. 8 is a schematic overview representing the principles of a method for analyzing the interaction between the proteins using the nanocluster formation according to still another embodiment of the present invention.

In another aspect of the present invention, a kit for analyzing interaction between proteins is provided, wherein the kit comprises: a first expression vector including a first gene construct containing a promoter and a first polynucleotide encoding a first fusion protein comprising a self-assembled protein, a first fluorescent protein and a light-induced heterodimerized protein, wherein the first polynucleotide is operably linked to the promoter; a second expression vector including a second gene construct containing a promoter, and a second polynucleotide encoding a second fusion protein comprising a partner protein interacting with the light-induced heterodimerized protein, a second fluorescent protein and a bait protein, wherein the second polynucleotide is operably linked to the promoter; and a third expression vector including a third gene construct containing a promoter and a third polynucleotide encoding a third fusion protein comprising a target protein which is a subject to be examined whether it interacts with the bait protein or not, and a third fluorescent protein, wherein the third polynucleotide is operably linked to the promoter;

with the proviso that all the fluorescent proteins emit different wavelengths of light and the first fluorescent protein may be omitted from the first fusion protein when the self-assembled protein is DsRed (FIG. 8).

In another aspect of the present invention, a kit for analyzing interaction between proteins is provided, wherein the kit comprises: a first expression vector including a first gene construct containing a promoter, a first polynucleotide encoding a first fusion protein comprising a self-assembled protein, a first fluorescent protein and a light-induced heterodimerized protein, wherein the first polynucleotide is operably linked to the promoter; a second expression vector including a second gene construct containing a promoter, a second polynucleotide encoding a second fusion protein comprising a partner protein interacting with the light-induced heterodimerized protein and a second fluorescent protein, and a multicloning site in which a polynucleotide encoding a bait protein is operably linked to the second polynucleotide, wherein the second polynucleotide is operably linked to the promoter; and a third expression vector including a third gene construct containing a promoter, a third polynucleotide encoding a third fusion protein comprising a third fluorescent protein, and a multicloning site in which a polynucleotide encoding a target protein which is a subject to be examined whether it interacts with the bait protein or not is operably linked to the third polynucleotide, wherein the third polynucleotide is operably linked to the promoter, with the proviso that all the fluorescent proteins emit different wavelengths of light and the first fluorescent protein may be omitted from the first fusion protein or the first fusion protein when the self-assembled protein is DsRed.

According to the kit, the first to third fluorescent proteins may be green fluorescent protein (GFP), yellow fluorescent protein (YFP), red fluorescent protein (RFP), orange fluorescent protein, cyan fluorescent protein (CFP), blue fluorescent protein (BFP), TagCFP, DsRed or tetracysteine fluorescent motif, independently.

According to the kit, the light-induced heterodimerized protein may be CIB, or CIBN.

According to the kit, the partner protein is a protein capable of forming a heterodimer with the light-induced protein by light irradiation and forming a homodimer regardless of light irradiation and may be CRY or PHR.

According to the kit, the self-assembled may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, the promoter may be a eukaryotic promoter.

As shown in FIG. 8, the present invention may be implemented by using a single nanoparticle comprising the light-induced heterodimerized protein capable of forming a homodimer regardless of light irradiation as well as forming a heterodimer with the partner protein by light irradiation and the self-assemble protein. Particularly, the embodiment of the present invention may be implemented by constructing the first expression vector capable of expressing the first fusion protein consisting of the self-assembled protein, the first fluorescent protein and the light-induced heterodimerized protein; the second expression vector capable of expressing the second fusion protein consisting of the partner protein interacting with the light-induced heterodimerized protein, the second fluorescent protein and a bait protein, and the third expression vector capable of expressing the third fusion protein consisting of the target protein to be examined whether it interacts with the bait protein or not and the third fluorescent protein. The light-induced heterodimerized protein capable of forming homodimer regardless of light irradiation may be CRY or PHR, an N-terminal fragment of the CRY, and the partner protein may be CIB or CIBN, an N-terminal fragment of CIB. If cells are cotransfected with the expression vectors and irradiating light having wavelengths capable of inducing heterodimerizing of the light-induced heterodimerized protein and the partner protein, light-induced nano-clusters are generated and in this case the fluorescent patterns by the first fluorescent protein and the second fluorescent protein are same with each other. In other words, the fluorescence emitted by the first fluorescent protein is displayed in a pattern of strong spots in the position where the corresponding fusion proteins are expressed according to the nano-cluster formation. In the meantime, the fluorescence emitted by the third fluorescent protein linked to the target protein is displayed differently depending on the interaction between the bait protein and the target protein. In other words, if the target protein interacts with the bait protein, the fluorescence emitted by the third fluorescent protein is displayed in the same pattern that emitted by the second fluorescent protein and if there is no interaction between the target protein and the bait protein, the fluorescent protein emitted by the third fluorescent protein will be displayed in a dispersed pattern in the position where the third fusion proteins are expressed after light irradiation.

In addition, the method of analyzing protein-protein interaction may be used for screening a substance regulating interprotein interaction, i.e. a substance promoting or inhibiting certain interprotein interaction. Life phenomena are represented by the result of an interprotein interaction, i.g. an interaction between a receptor and a ligand binding thereto and an abnormal interaction between these proteins may result in pathological condition. Therefore, the kit and method of the present invention may be used as a kit and method for screening of therapeutic candidates in cellular level efficiently.

Indeed, the present inventors co-expressed a fusion protein in which CIBN is fused to an activation domain (AD) of CalMKIIα, a fusion protein in which PHR is fused to Hras, and $RBD_{raf1}$ in cells and irradiated blue light having 488 nm which induces the interaction between CIBN and PHR. As a result, the interaction between Hras and $RBD_{raf1}$ was confirmed by analyzing of fluorescence pattern shown in the cells (See FIG. 18).

In another aspect to the present invention, a method for inhibiting a target protein reversibly using light-induced protein nano-cluster formation is provided, wherein the method comprises: co-expressing a fusion protein comprising a self-assembled protein and a light-induced heterodimerized protein, a partner protein capable of heterodimerizing with light-induced heterodimerized protein, and a bait protein interacting with a target protein in a cell or a subject expressing the target protein as an inherent protein; and inducing a protein nano-cluster formation by irradiating light having wavelength capable of inducing heterodimerizing between the light-induced heterodimerized protein and the partner protein to the cell or the subject According to the method, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the method, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the method, the light-induced heterodimerized protein may be CIB, CIBN, PhyB, PIF, FKF1, GIGANTEA, CRY, or PHR.

According to the method, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may a protein capable of forming a heterodimer with the light-induced protein by light irradiation and forming a homodimer regardless of light irradiation. In this case the light-induced heterodimerized protein or the partner protein may be CRY or PHR.

In another aspect of the present invention, a method for inhibiting a target protein reversibly using light-induced protein nano-cluster formation is provided, wherein the method comprises: co-expressing a first fusion protein comprising a first self-assembled protein and a light-induced heterodimerized protein, a second fusion protein comprising a second self-assembled protein and a partner protein capable of heterodimerizing with the light-induced heterodimerized protein, and a bait protein interacting with a target protein in a cell or a subject expressing the target protein as an inherent protein; and inducing a protein nano-cluster formation by irradiating light having wavelength capable of inducing heterodimerizing between the light-induced heterodimerized protein and the partner protein to the cell or the subject, wherein the bait protein is expressed as a fusion protein with the first self-assembled protein or the second self-assembled protein.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus). In this case, when the first self-assembled protein and the second self-assembled protein are used at the same time, the first self-assembled protein and the second self-assembled protein may be same or different According to the method, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the method, the light-induced heterodimerized protein may be CIB, CIBN, PhyB, PIF, FKF1, GIGANTEA, CRY, or PHR.

According to the method, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may form a homodimer regardless of light irradiation by itself. In this case the light-induced heterodimerized protein or the partner protein may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter, and a second polynucleotide encoding a partner protein capable of heterodimerizing with light-induced heterodimerized protein, wherein the second polynucleotide is operably linked to the promoter; and a third expression vector including a third gene construct containing a promoter and a third polynucleotide encoding a bait protein interacting with the target protein, wherein the third polynucleotide is operably linked to the promoter, wherein the bait protein is expressed as a fusion protein with the self-assembled protein or the partner protein.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may form a homodimer regardless of light irradiation by itself. In this case the light-induced heterodimerized protein or the partner protein may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a first fusion protein comprising a first self-assembled protein and a light-induced heterodimerized protein, wherein the first polynucleotide is operably linked to the promoter; a second expression vector including a second gene construct containing a promoter and a second polynucleotide encoding a second fusion protein comprising a second self-assembled protein and a partner protein capable of heterodimerizing with the light-induced heterodimerized protein, wherein the second polynucleotide is operably linked to the promoter; and a third expression vector including a third gene construct containing a promoter and a multicloning site for inserting a third polynucleotide encoding a bait protein interacting with the target protein, wherein the third polynucleotide is operably linked to the promoter, and wherein the bait protein is expressed as a fusion protein with the self-assembled protein or the partner protein.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may form a homodimer regardless of light irradiation by itself. In this case the light-induced heterodimerized protein or the partner protein may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter and a second polynucleotide encoding a partner protein capable of heterodimerizing with the light-induced heterodimerized protein, wherein the second polynucleotide is operably linked to the promoter; and a third expression vector including a third gene construct containing a promoter and a multicloning site for inserting a third polynucleotide encoding a bait protein interacting with the target protein, wherein the third polynucleotide is operably linked to the promoter, wherein the bait protein is expressed as a fusion protein with the self-assembled protein or the partner protein.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may form a homodimer regardless of light irradiation by itself. In this case the light-induced heterodimerized protein or the partner protein may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a first fusion protein comprising a first self-assembled protein and a light-induced heterodimerized protein, wherein the first polynucleotide is operably linked to the promoter; a second expression vector including a second gene construct containing a promoter and a second polynucleotide encoding a second fusion protein comprising a second self-assembled protein and a partner protein capable of heterodimerizing with the light-induced heterodimerized protein, wherein the second polynucleotide is operably linked to the promoter; and a third expression vector including a third gene construct comprising a promoter and a third polynucleotide encoding a bait protein interacting with the target protein, wherein the third polynucleotide is operably linked to the promoter, wherein the bait protein is expressed as a fusion protein with the first self-assembled protein or the second self-assembled protein.

According to the kit, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangenne. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyBC or the partner protein may be FKF1 when the light-induced heterodimerized protein is GIGANTEA. The PIF may be PIF3 or PIF6.

According to the kit, the light-induced heterodimerized protein or the partner protein may form a homodimer regardless of light irradiation by itself. In this case the light-induced heterodimerized protein or the partner protein may be CRY or PHR.

In an aspect of the present invention, a method for inhibiting a target protein reversibly using light-induced nanocluster formation, wherein the method comprises: co-expressing a first fusion protein including self-assembled protein and a light-induced heterodimerzable protein, a partner protein forming a heterodimer with the light-induced heterodimerzable protein, and a target protein in a cell or a subject; and inducing light-induced formation of nanocluster by irradiating light having wavelength capable of forming the heterodimer between the light-induced heterodimerized protein and the partner protein, wherein the target protein is expressed as a fusion protein with the self-assembled protein or the partner protein.

According to the method, the first self-assembled protein and the second self-assembled protein may be independently ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the method, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer or mTangerine. The cyan fluorescent protein may be ECFP, mECFP, mCerulean, CyPet. AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the method, the light-induced heterodimerized protein may be CIB, CIBN, PhyB, PIF, FKF1, GIGANTEA, CRY, or PHR.

According to the method, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN. PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the method, the light-induced heterodimerized protein or the partner protein may form a homodimer regardless of light irradiation by itself. In this case the light-induced heterodimerized protein or the partner protein may be CRY or PHR.

In another aspect of the present invention, a kit for inhibiting a target protein reversibly using light-induced protein nano-cluster formation is provided, wherein the kit comprises: a first expression vector including a first gene construct containing a promoter and a first polynucleotide encoding a fusion protein comprising a self-assembled protein and a light-induced heterodimerized protein, wherein the first polynucleotide is operably linked to the promoter; a second expression vector including a second gene construct containing a promoter and a second polynucleotide encoding a second fusion protein comprising a partner protein capable of heterodimerizing with the light-induced heterodimerized protein, wherein the second polynucleotide is operably linked to the promoter; and optionally a third expression vector including a third gene construct containing a promoter and a third polynucleotide encoding a third fusion protein containing the target protein and the self-assembled protein, wherein the third polynucleotide is linked operably to the promoter, or wherein the target protein is included in the second fusion protein instead of comprising the third polynucleotide.

According to the kit, the self-assembled protein may be ferritin, virus capsid protein, ferritin-like protein, calcium/calmodulin-dependent protein kinase II alpha subunit (CaMKIIα) or DsRed and the virus capsid protein may be a capsid protein derived from CCMV (cowpea chlorotic mottle virus), Norwalk virus, SV40, or HPV (human papilloma virus).

According to the kit, at least one protein among the fusion protein, the partner protein and the bait protein may further comprise a fluorescent protein in order to determine whether the nano-cluster is generated or not. In this case, the fluorescent protein may be green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif. The green fluorescent protein may be EGFP, Emerald, Superfolder GFP, Azami Green, TagGFP, TurboGFP, ZsGreen or T-Sapphire. The yellow fluorescent protein may be EYFP, Topaz, Venus, mCitrine, Ypet, TagYFP, PhiYFP, mBanana, or ZsYellow1. The red fluorescent protein may be mRuby, mApple, mStrawberry, AsRed2 or mRFP. The orange fluorescent protein may be Kusabira Orange, Kusabira Orange2, mOrange, mOrange2, dTomato, dTomato-Tandem, TagRFP, TagRFP-T, DsRed. DsRed2, DsRed-Express, DsRed-Monomer or mTangerine. The cyan fluorescent protein may be ECFP, mECFP, mCerulean, CyPet, AmCyan1, Midori-Ishi Cyan, TagCFP, or mTFP1. The blue fluorescent protein may be EBFP, EBFP2, Azurite or mTagBFP. The far red fluorescent protein may be mPlum, mCherry, the dKeima-Tandem, JRed, mRaspberry, HcRed1, HcRed-Tandem, or AQ143. The tetracysteine fluorescent motif may be a polypeptide including an amino acid sequence of Cys-Cys-Xaa-Xaa-Xaa-Cys-Cys (SEQ ID NO: 1), wherein the Xaa is one of any amino acids except cysteine.

According to the kit, the light-induced heterodimerized protein may be CIB, CIBN, PhyB, PIF, FKF1, GIGANTEA, CRY, or PHR.

According to the kit, the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB, CIBN, PhyB, PIF, FKF1, GIGANTEA, CRY, or PHR, and the partner protein may be CRY or PHR when the light-induced heterodimerized protein is CIB or CIBN, the partner protein may be PIF when the light-induced heterodimerized protein is PhyB, the partner protein may be GIFANTEA when the light-induced heterodimerized protein is FKF1, the partner protein may be CIB or CIBN when the light-induced heterodimerized protein is CRY or PHR, the partner protein may be PIF when the light-induced heterodimerized protein is PhyB, or the partner protein may be FKF1 when the light-induced heterodimerized protein is GIGANTEA. The PIF may be PIF3 or PIF6.

According to the kit, the light-induced heterodimerized protein or the partner protein may form a homodimer regardless of light irradiation by itself. In this case the light-induced heterodimerized protein or the partner protein may be CRY or PHR.

The methods and kits for inhibiting function of a protein reversibly are hereinafter described in more detail by accompanying drawings.

Figure 9:
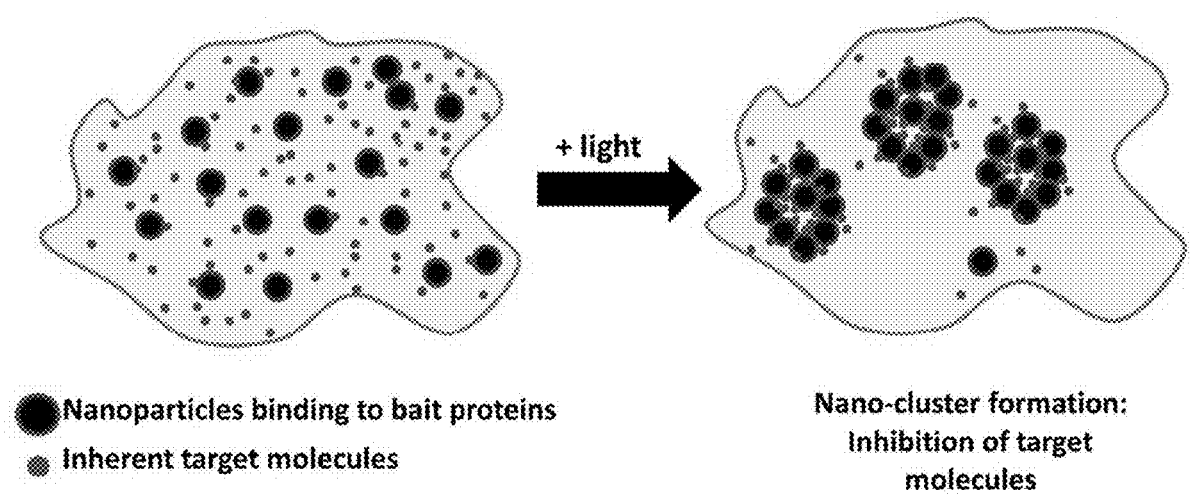
FIG. 9 is a schematic overview representing the principles of a method for inhibiting a target protein using the nanocluster formation according to an embodiment of the present invention.

FIG. 9 is a schematic overview representing the principles of a method for inhibiting a target protein using the nanocluster formation according to an embodiment of the present invention. When nanoparticles containing a bait protein and a light-induced heterodimerized protein and a partner protein forming a heterodimer with the light-induced heterodimrized protein by light irradiation are co-expressed in a cell and light having wavelength capable of inducing the formation of a heterodimer between the light-induced heterodimerized protein and the partner protein is irradiated and nano-clusters are generated thereby, the target protein captured by the bait protein are confined in the nano-clusters.

Figure 10:
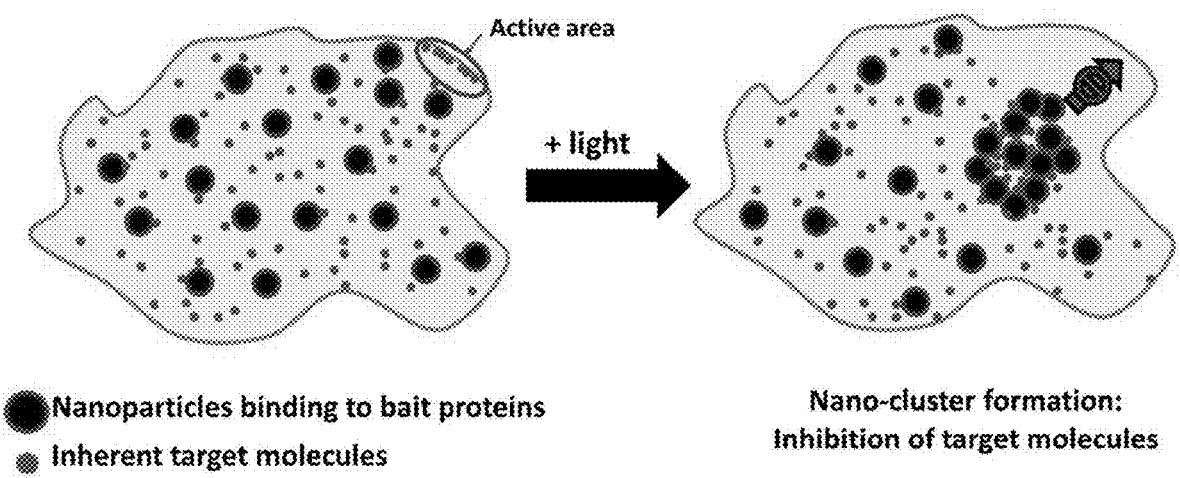
FIG. 10 is a schematic overview representing the principles of the inhibition of a particular protein by entrapment of the target protein interacting with a partner protein via the formation of nanoclusters between the two proteins by irradiating light having a particular wavelength within partial active region of a cell.

FIG. 10 is a schematic overiew representing the principles of the inhibition of a particular protein by entrapment of the target protein interacting with a partner protein via the formation of nanoclusters between the two proteins by irradiating light having a particular wavelength within partial active region of a cell. Since only a particular region in a cell may be irradiated using laser beam, the method of the present invention may be used for examining effect on inhibiting function of a protein in a particular region of a cell usefully.

Figure 11:
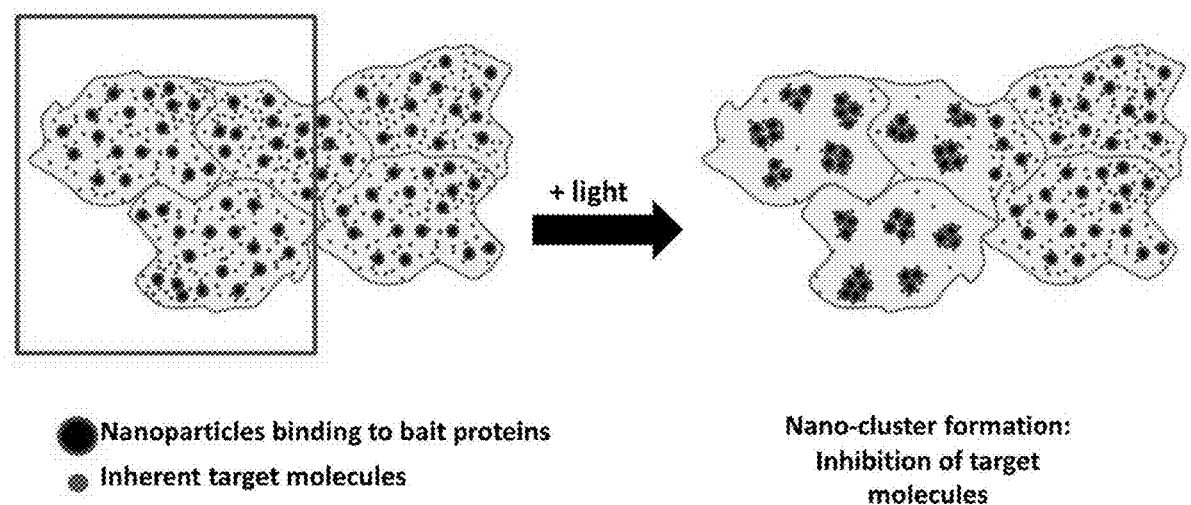
FIG. 11 is a schematic overview representing the principles of the formation of nanoclusters within multicellular area such as a subject and a tissue and the inhibition of a particular protein within the area by irradiating light having a particular wavelength to area.

FIG. 11 is a schematic overview representing the principles of the formation of nanoclusters within multicellular area such as a subject and a tissue and the inhibition of a particular protein within the area by irradiating light having a particular wavelength to area. The method of the present invention is a very useful method with regard to being capable of observing comparatively changes of an experimental group and a control group after light irradiation.

Figure 12:
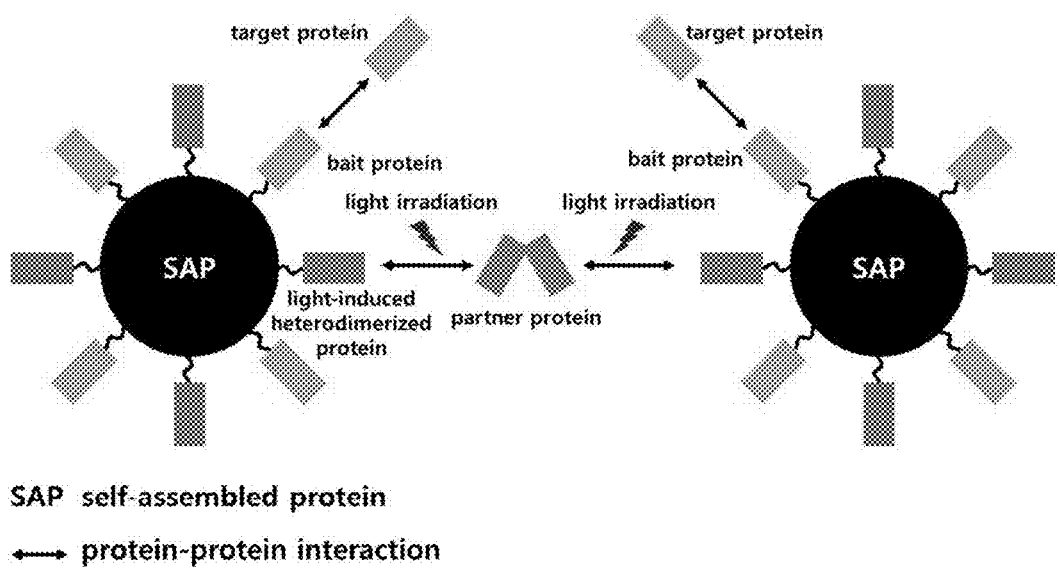
FIG. 12 is a schematic diagram illustrating conceptually the formation of nano-clusters and the regulation of molecular function of a particular protein thereby by light irradiation in accordance with an embodiment of the present invention.

FIG. 12 is a schematic diagram illustrating conceptually the formation of nano-clusters and the regulation of molecular function of a particular protein thereby by light irradiation in accordance with an embodiment of the present invention. As shown in FIG. 12, the nanoparticle is a hetero-complex generated by self-assembly of a fusion protein comprising a self-assembled protein (SAP) and a light-induced heterodimerized protein (e.g., CIBN), and a fusion protein comprising the self-assembled protein and a bait protein and the bait protein takes a role as a bait for confining a target protein expressed inherently in a cell and the light-induced heterodimerized proteins form nano-clusters by interacting with partner proteins forming homodimers (e.g. PHR) and the target proteins captured by the bait proteins are confined within the nano-clusters.

Figure 13:
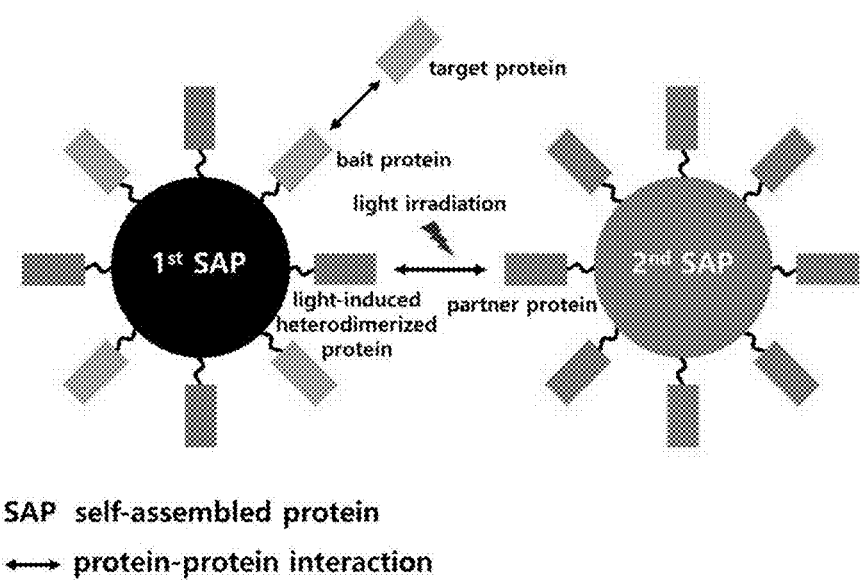
FIG. 13 is a schematic diagram illustrating conceptually the formation of nano-clusters by irradiating two different nanoparticles and a method for regulating molecular function of a particular protein thereby according to an embodiment of the present invention.

FIG. 13 is a schematic diagram illustrating conceptually the formation of nano-clusters by irradiating two different nanoparticles and a method for regulating molecular function of a particular protein thereby according to an embodiment of the present invention. In this case, the first nanoparticle is generated as a heterocomplex self-assembled by the first fusion protein including the first self-assembled protein and a light-induced heterodimerized protein, and the second fusion protein including the first self-assembled protein and the bait protein, and the second nanoparticle is generated by self-assembly of the third fusion protein including the second self-assembled protein and the partner protein interacting with the light-induced heterodimerized protein. If the light-induced heterodimerized protein and the partner protein displayed on the surface of the first nanoparticle and the second nanoparticle respectively interact each other by light irradiation and a nano-cluster is generated, the target protein captured by the bait protein is confined within the nano-cluster.

Figure 14:
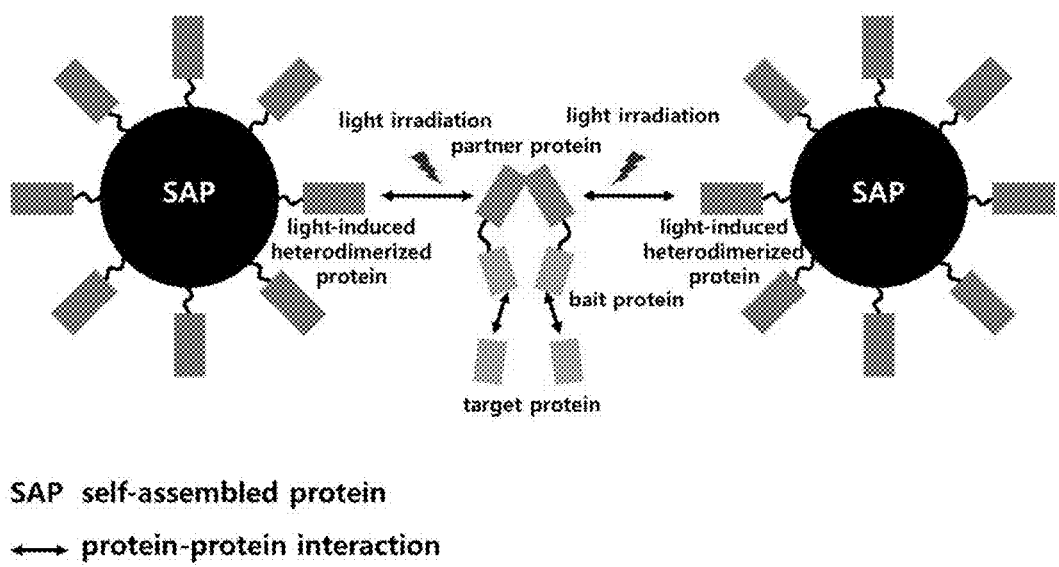
FIG. 14 is a schematic diagram illustrating conceptually the formation of nano-clusters by irradiating and a method for regulating molecular function of a particular protein thereby according to another embodiment of the present invention.

FIG. 14 is a schematic diagram illustrating conceptually the formation of nano-clusters by irradiating and a method for regulating molecular function of a particular protein thereby according to another embodiment of the present invention. In this case, the nanoparticle is a homocomplex generated by self-assembly of a first fusion protein including the self-assembled protein (SAP) and the light-induced heterodimerized protein, and a nanocluster is generated when a light having wavelength capable of inducing heterodimerization between the light-induced heterodimerized protein and the partner protein after co-expressing the first fusion protein and the second fusion protein including the partner protein interacting with the light-induced heterodimerized protein and a bait protein in a cell. As a result, the target protein which is an inherent protein in the cell is captured by the bait protein and is confined within the nano-cluster thereby.

Figure 15:
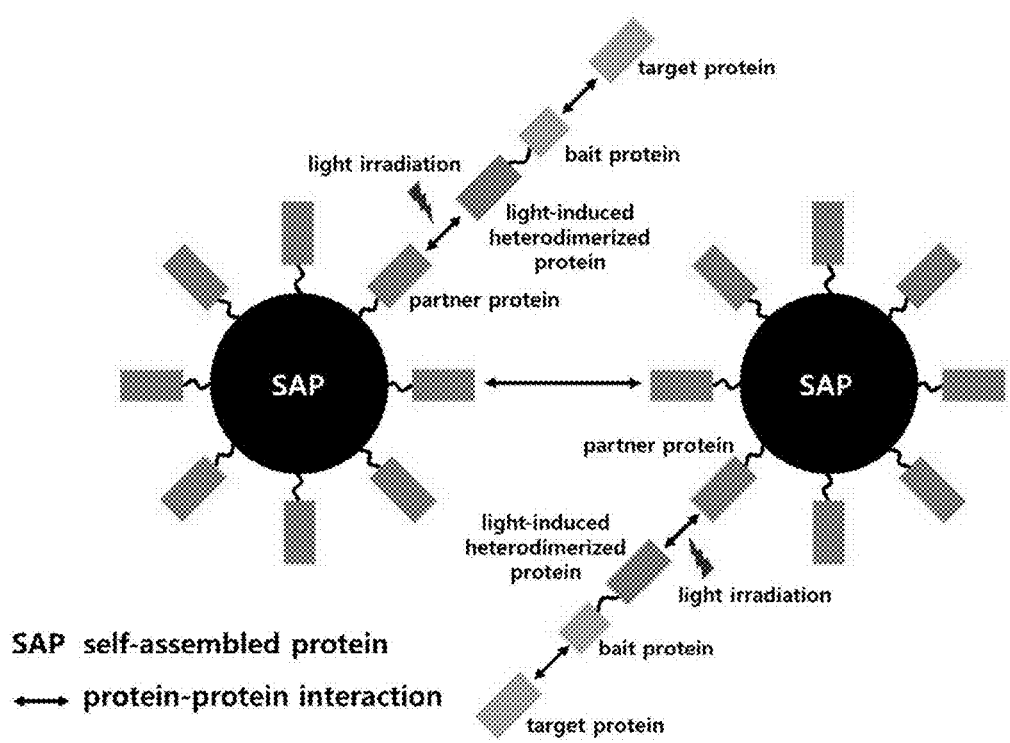
FIG. 15 is a schematic diagram illustrating conceptually the formation of nano-clusters by irradiating and a method for regulating molecular function of a particular protein thereby according to still another embodiment of the present invention.

FIG. 15 is a schematic diagram illustrating conceptually the formation of nano-clusters by irradiating and a method for regulating molecular function of a particular protein thereby according to still another embodiment of the present invention. As shown in FIG. 15, the nanoparticle is a homocomplex generated by self-assembly of a first fusion protein including a self-assembled protein and a light-induced heterodimerized protein forming a homodimer regardless of light irradiation (e.g., PHR), and if heterodimerization between the light-induced heterodimerized protein and the partner protein is induced by light irradiation after co-expressing the first fusion protein and the second fusion protein including the partner protein interacting with the light-induced heterodimerized protein and a bait protein in a cell. As a result, the target protein which is an inherent protein in the cell is captured by the bait protein and is confined within the nano-cluster thereby.

Figure 16:
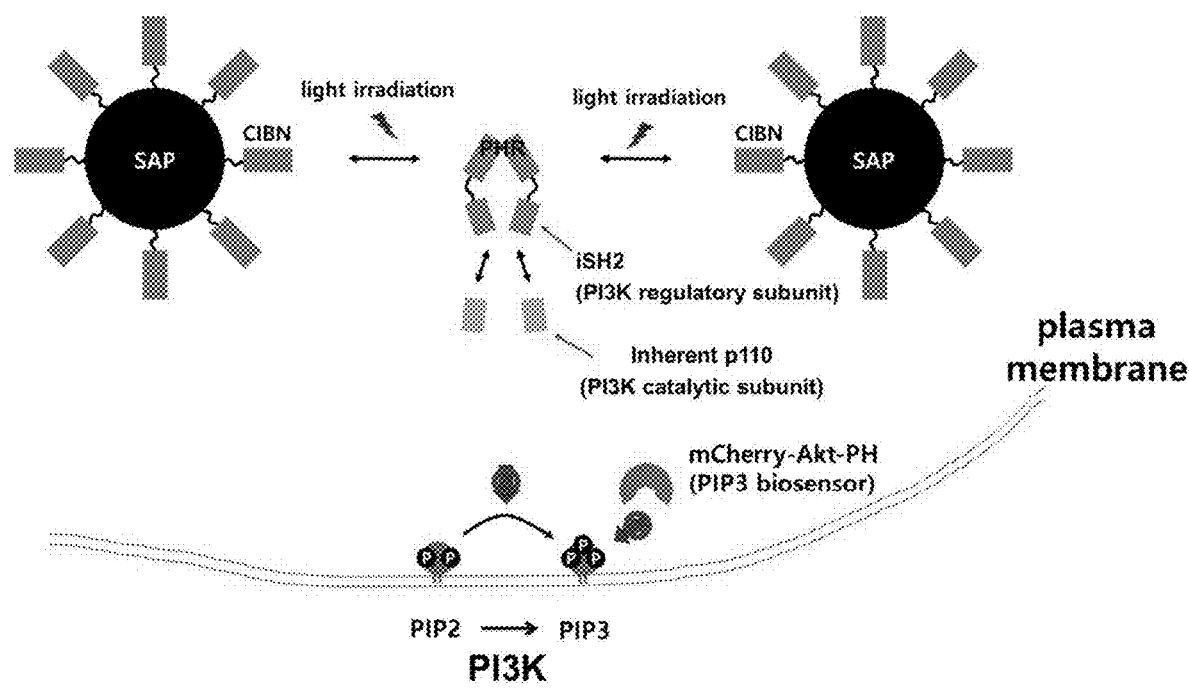
FIG. 16 is a schematic diagram illustrating conceptually the formation of nano-clusters by irradiating and the regulation of function of PI3K protein using the method illustrated in FIG. 14 according to an embodiment of the present invention.

FIG. 16 is a schematic diagram illustrating conceptually the formation of nano-clusters by irradiating and the regulation of function of PI3K protein using the method illustrated in FIG. 14 according to an embodiment of the present invention.

Figure 17:
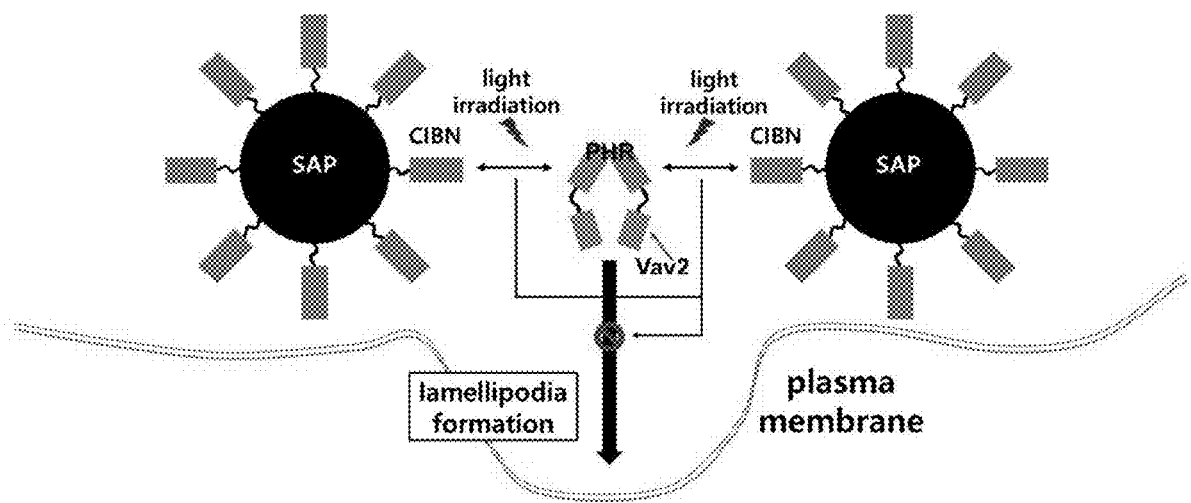
FIG. 17 is a schematic diagram illustrating conceptually the formation of nano-clusters by irradiating according to an embodiment of the present invention and the regulation of function of Vav2 protein using the same.

FIG. 17 is a schematic diagram illustrating conceptually the formation of nano-clusters by irradiating according to an embodiment of the present invention and the regulation of function of Vav2 protein using the same. An intracellular protein, p110 (PI3K catalytic subunit) phosphorylates a substrate attached to cell membrane, PIP2 (phosphatidyl-inositol-3,4-bisphosphate) when a growth factor such as PDGF (platelet-derived growth factor) is treated to a cell. If PIP3 (phosphatidyl-inosito-3,4,5-triphosphate) is generated by the phosphorylation of PIP2, a PIP3 biosensor, PH domain of Akt protein existing in cytoplasm translocates to cell membrane by recognizing the resulting PIP3. However, the phosphorylation of PIP2 is inhibited and the translocation of the PH domain to cell membrane may be inhibited thereby if p110 is captured by iSH2 (inter Src homology 2 domain), a PI3K regulatory subunit as a bait protein by the photo-induced nano-cluster formation and confined within a nano-cluster thereby.

Figure 19:
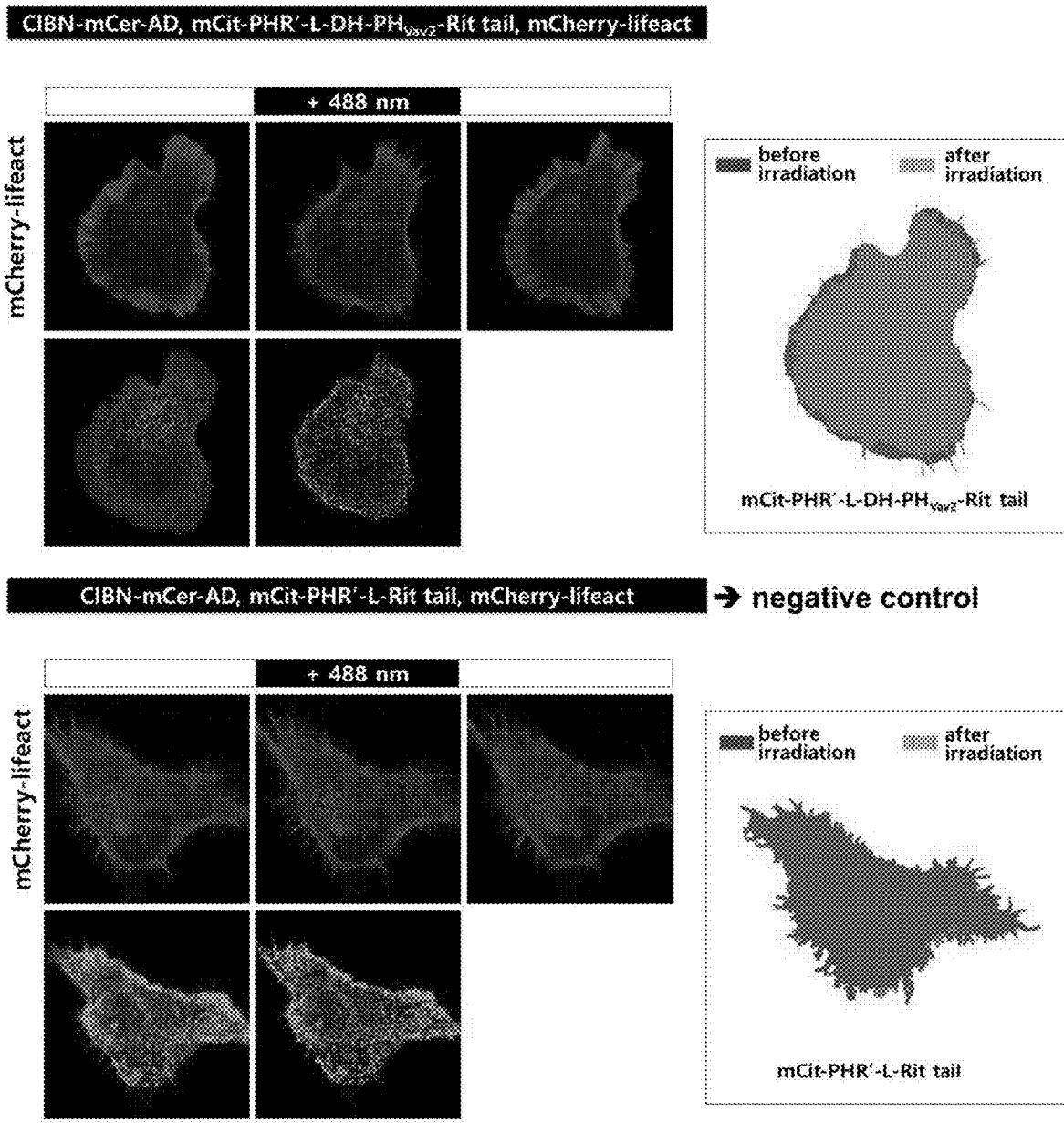
FIG. 19 is a fluorescent microscophic photograph showing the result of the formation of nano-clusters by light irradiation and the inhibition of a particular protein over a period of time thereby, which proves the conception illustrated in FIG. 17.

The present inventors confirmed experimentally that nanoclusters were generated due to the interaction between nanoparticles containing CIBN (N-terminal of cryptochrome-interacting basic-helix-loop-helix) forming a light-induced heterodimer with PHR (photolyase homologous region of cryptochrome 2) and the PHR, and Vav2 proteins were captured within the nanoclusters and the formation of lamellipodia which is induced by the Vav2 proteins was inhibited thereby, when a fusion protein containing an association domain (AD) of CaMKIIα involving in self-assembly and the CIBN, and a fusion protein containing the PHR and the Vav2 protein (a target protein) were co-expressed in a cell and nanoparticles were generated by the self-assembly of the AD of CaMKIIα and blue light with 488 nm of wavelength capable of forming the heterodimer between the CIBN and the PHR was irradiated (See FIG. 19). On the other hand, if a gene construct lacking a gene encoding the target protein (Vav2 protein) was used, the nanoclusters were generated but the formation of the lamellipodia was not affected. (See FIG. 19). Therefore, the methods and kits according to the present invention are useful tools for regulating a particular protein expressed or inherent in a cell and biochemically related downstream proteins effectively and in a reversible manner.

MODE FOR INVENTION

Example 1: Construction of Vectors 1-1: Preparation of CIBN-CFP-AD Constructs

The present inventors constructed a polynucleotide encoding a fusion protein in which CFP (cyan fluorescent protein) and an N-terminal (1-170 a.a.) of CIB1 (cryptochrome-interacting basic-helix-loop-helix, GenBank No.: NM_119618) is serially fused to N-terminal of AD (315-478 a.a.) of CaMKIIα (GenBank No.: NM_012920) involving in self-assembly of the CaMIIα, and thus constructed resulting a CIBN-CFP-AD construct by inserting the polynucleotide into a pCFP-C1 vector replacing a polynucleotide encoding CFP of the vector with the polynucleotide encoding the fusion protein (FIG. 1.).

1-2: Preparation of $PHR_{CRY2}$-mCherry Construct

A polynucleotide encoding a polypeptide fragment (1-498 a.a.) corresponding PHR (phytolyase homologous region) domain of CYR2 protein (GenBank No. NM_100320) was inserted into pmCherry-N1 vector (Clontech, USA) and the resulting PHRCRY2-mCherry construct was prepared thereby. The CRY protein and the PHR form a heterodimer when expressed in a cell (FIG. 1).

Example 2: Preparation of Vectors for Analyzing Protein Interaction

The present inventors constructed expression vectors capable of expressing a bait protein and a target protein as described below, in order to investigate whether the method for analyzing protein interaction using the light-induced nanocluster formation may be used for analyzing the interaction between other proteins based on the result of example 1.

2-1: Preparation of PHR-CCF)-Hras(Active) Construct

The present inventors constructed PHR-ECFP-Hras(active) construct by producing a polynucleotide encoding a fusion protein in which the PHR domain (1-498 a.a.) of CRY2 (GenBank No.: NM_100320) and a bait protein, active form Hras (GenBank No.: NM_001130442.1, Q61L mutant, CAAX-deleted) are fused to N-temnal and C-terminal of ECFP, respectively and inserting the polynucleotide into pECFP-C1 vector (Clontech, USA).

2-2: Preparation of YFP-$RBD_{raf1}$ Construct

The present inventors constructed YFP-$RBD_{raf1}$ construct by inserting operably a polynucleotide encoding Ras binding domain ($RBD_{raf1}$, 51-131 a.a.) of Raf1 (GenBank No.; NM_002880.3) into a 3'-end of a polynucleotide encoding YFP of pYFP vector (Clontech, USA).

2-3: Preparation of YFP-$RBD_{p110}$ Construct

The present inventors constructed YFP-$RBD_{p110}$ construct by inserting a polynucleotide encoding Ras binding domain ($RBD_{p110}$, 133-332 a.a.) of p110 alpha (GenBank No.: NM_006218.2) into a 3'-end of a polynucleotide encoding YFP of pYFP (Clontech, USA).

2-4: Preparation of PHR-ECFP-Hras(Inactive) Construct

PHR-ECFP-Hras(inactive) construct was constructed by substituting Hras(active) gene with Hras(inactive) gene (S17N mutant, CAAX-deleted) in the PHR-ECFP-Hras(active) construct prepared in example 2-1.

2-5: Preparation of YFP-$CRIB_{PAK1}$ Construct pYFP-$CRIB_{PAK1}$ construct was constructed by substituting $RBD_{p110}$ gene with $CRIB_{PAK1}$ gene (GenBank No.: NM_001128620.1, 69-108 a.a.) in the YFP-$RBD_{p110}$ construct prepared in example 2-3.

Example 3: Construction of Vectors for Inhibiting a Protein Reversibly 3-1: Preparation of CIBN-mCerulean-AD Construct CIBN-mCerulean-AD construct was constructed by inserting a polynucleotide encoding a fusion protein in which a cyan fluorescent protein (mCerulean) and an N-terminal (1-170 a.a.) of CIB1 protein participating in light-induced heterodimerizing are serially fused to the N-terminal of activation domain (315-478 a.a.) into pmCerulean-C1 vector (Clontech, USA) instead of the polynucleotide encoding the mCerulean.

3-2: Preparation of mCitrine-$PHR_{CRY2}$ Construct mCitrine-$PHR_{CRY2}$ construct was constructed by inserting a polynucleotide encoding a polypeptide corresponding to the PHR of CYR2 protein (1-498 a.a. of CRY2) into pmCitrine-C1 vector (Clontech, USA).

3-3: Preparation of mCitrine-$PHR_{CRY2}$-Rit Tail Construct mCitrine-$PHR_{CYR2}$-Rit tail construct was constructed by inserting a polynucleotide encoding a tail domain (193-219 a.a.) of Rit (GenBank No.: NM_006912) which is localized to plasma membrane into the mCitrine-$PHR_{CYR2}$ construct whereby the Rit tail is fused to the C-terminal of PHR. The Rit tail is a protein capable of attaching electrically to phospholipid molecules having negative charge and capturing a protein in the plasma membrane.

3-4: Preparation of mCitrine-$PHR_{CRY2}$-$DHPH_{Vav2}$-Rit Tail Construct mCitrine-$PHR_{CRY2}$-$DHPH_{Vav2}$-Rit tail construct was constructed by inserting a polynucleotide encoding a fusion protein in which a polypeptide corresponding a PHR domain (1-498 a.a.) of CRY2 (GenBank No.: NM_100320), a DH-PH domain (167-541 a.a.) of Vav2 (GenBank No.: NM_001134398) inducing the formation of lamellipodia as a target protein and a tail domain (193-219 a.a.) of Rit (GenBank No.: NM_006912) are serially fused to the C-terminal of the mCitrine into pmCitrine-C1 vector (Clontech, USA). Since the Vav2 protein has PH domain and may activate proteins localized in plasma membrane by translocating into plasma membrane weakly, it may perform recruiting of a protein into plasma membrane. However, the present inventors used a Rit tail construct in order to recruit Vav2 protein into plasma membrane clearly.

3-5: Preparation of mCherry-Lifeact Construct mCherry-lifeact construct was constructed by inserting a polyncleotide encoding lifeact, a marker for visualizing F-actin, which consists of an N-terminal fragment (1-17 a.a.) of Abp140 (actin binding protein 140, GenBank No.: NM_001183658) into pmCherry-C1 vector (Clontech, USA).

Experimental Example 1: Investigation of Light-Induced Nanocluster Formation

The present inventors observed intracellular fluorescent patterns of Cos-7 cells (ATCC no. CRL-1651) co-transfected with the CIBN-RFP-FT construct and the CRY2 construct prepared by the example 1 irradiated with blue light having 488 nm of wavelength using pulsed irradiation (for total 5 secs with 1 sec per irradiation at an interval of 12 secs). As a result, when the blue light was irradiated, red fluorescence dispersed within cytosol was displayed in a pattern including a plurality of strong red dots and then was dispersed in the cytosol again over time (FIG. 2). Although analyzing the phenomenon as the number of strong red dots, the number got increased when the blue light was irradiated and got decreased gradually over time (FIG. 3). Therefore, the present inventors proved that a nanoparticle generated by self-assembly of a fusion protein including a light-induced heterodimerized protein and a self-assembled protein may be clustered by the interaction of the light-induced heterodimerized protein and a partner protein capable of heterodimerizing with the light-induced heterodimerized protein by light irradiation and then be visualized by fluorescent proteins.

Experimental Example 2: Analysis of Protein-Protein Interaction 2-1: Co-Transfection of CIBN-RFP-AD, PHR-ECFP-Hras(Active) and YFP-RBD$_{raf1}$ Constructs The CIBN-RFP-AD construct prepared in the example 1-1, the PHR-CFP-Hras(active) construct prepared in the example 2-1 and the YFP-RBD$_{raf1}$ construct prepared in the example 2-2 were co-transfected into Cos-7 cells (ATCC No. CRL-1651) using electroporation method (1,000 V, 35 ms, 2 pulse) and fusion proteins were expressed by cultivating the transected cells for 24 hour which were plated on 96-well glass bottom plate (Matrical Bioscience, USA) in a incubator under the condition of 10% $CO_2$ and 37° C.

2-2: Co-Transfection of CIBN-RFP-AD, PHR-ECFP-Hras(Active) and YFP-RBD$_{p110}$ Constructs The CIBN-RFP-AD construct prepared in the example 1-1, the PHR-CFP-Hras(active) construct prepared in the example 2-1 and the YFP-RBD$_{p110}$ construct prepared in the example 2-3 were co-transfected into Cos-7 cells (ATCC No. CRL-1651) using electroporation method (1,000 V, 35 ms, 2 pulse) and fusion proteins were expressed by cultivating the transfected cells for 24 hour which were plated on 96-well glass bottom plate (Matrical Bioscience, USA) in a incubator under the condition of 10% $CO_2$ and 37° C.

2-3: Co-Transfection of CIBN-RFP-AD, PHR-ECFP-Hras(Inactive) and YFP-RBD$_{raf1}$ Constructs The CIBN-RFP-AD construct prepared in the example 1-1, the PHR-CFP-Hras(inactive) construct prepared in the example 2-4 as a negative control and the YFP-RBD$_{raf1}$ construct prepared in the example 2-2 were co-transfected into Cos-7 cells (ATCC No. CRL-1651) using electroporation method (1,000 V, 35 ms, 2 pulse) and fusion proteins were expressed by cultivating the transfected cells for 24 hour which were plated on 96-well glass bottom plate (Matrical Bioscience, USA) in a incubator under the condition of 10% $CO_2$ and 37° C.

2-4: Co-Transfection of CIBN-RFP-AD, PHR-ECFP-Hras(Active) and YFP-CRIB$_{PAK1}$ Constructs The CIBN-RFP-AD construct prepared in the example 1-1, the PHR-CFP-Hras(active) construct prepared in the example 2-1 and the YFP-CRIB$_{PAK1}$ construct prepared in the example 2-5 as another negative control were co-transfected into Cos-7 cells (ATCC No. CRL-1651) using electroporation method (1,000 V. 35 ms, 2 pulse) and fusion proteins were expressed by cultivating the transfected cells for 24 hour which were plated on 96-well glass bottom plate (Matrical Bioscience, USA) in a incubator under the condition of 10% $CO_2$ and 37° C.

2-5: Analysis of Nanocluster Formation by Light Irradiation

Figure 18:
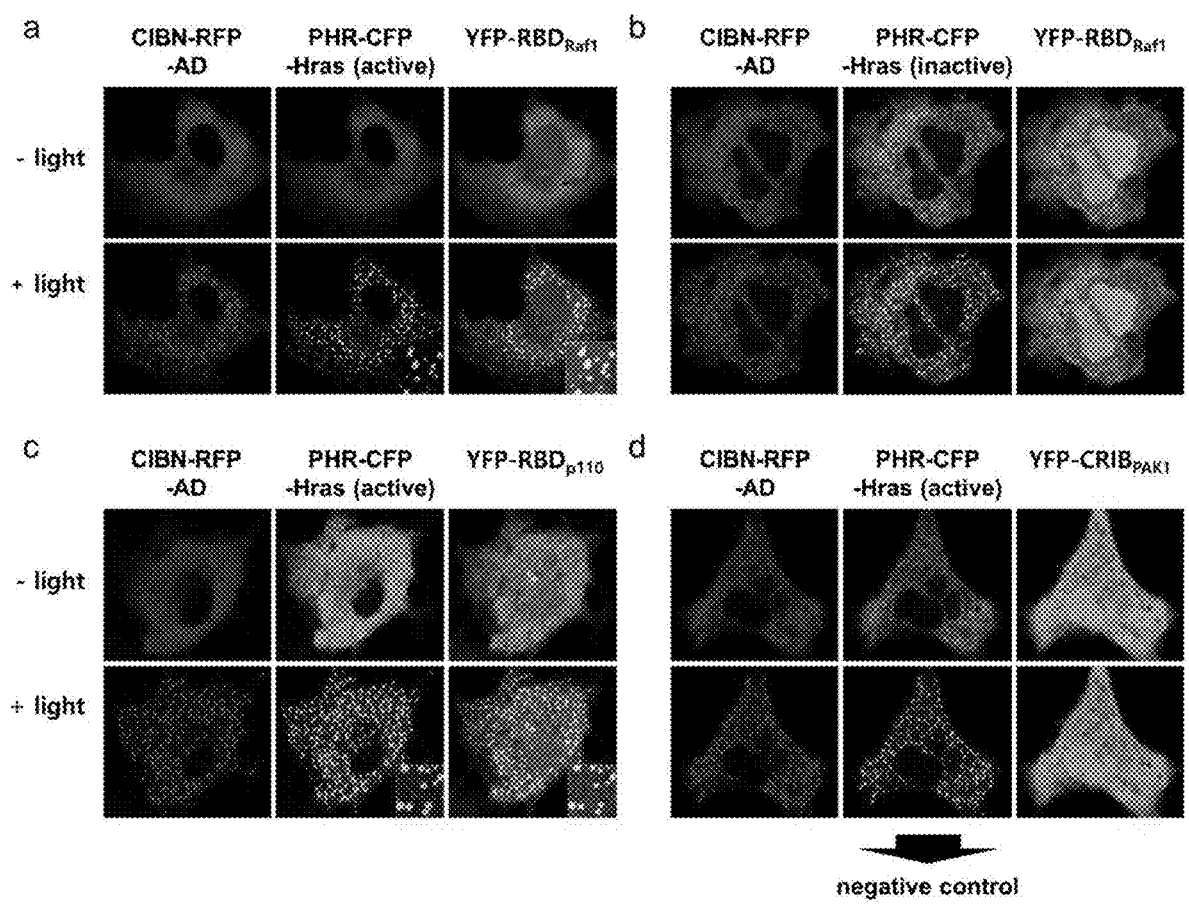
FIG. 18 is a fluorescent microscophic photograph representing experimental results showing interactions between Hras and RBD raf1, and Hras and RBD p110, respectively using a method for analyzing the interaction between proteins using the nano-cluster formation according to an embodiment of the present invention.

The present inventors observed fluorescent patter within cells co-transfected in the above experimental examples 2-1 to 2-4 after irradiating blue light having 488 nm of wavelength capable of inducing the interaction between CIBN and CRY2 using pulsed irradiation (for total 7 secs with 1 sec per irradiation at an interval of 10 secs) (FIG. 18). As a result, when cells co-transfected with the CIBN-RFP-AD construct, the PHR-ECFP-Hras(active) construct and the YFP-RBDraf1 construct were irradiated with blue light, patterns of red, cyan and yellow fluorescence shifted from dispersed ones to strong dotted ones and the locations of fluorescence for each color were same and thus it was confirmed that the fluorescent proteins emitting each color were co-located (FIG. 18a). This means that nanoparticles generated by AD of CalMKIIα, a self-assembled protein formed nano-clusters due to intermolecular interaction and it proves that the PHR-ECFP-Hra(active) fusion protein forming a homodimer interacted with the CIBN-RFP-AD fusion protein forming a self-assembled nanoparticle and Hras (active) which is used as a bait protein interacted with RBD$_{raf1}$, a target protein.

In addition, when cells co-transfected with the CIBN-RFP-AD construct, PHR-ECFP-Hras(active) construct and the YFP-RBD$_{p110}$ were irradiated with blue light, patterns of red, cyan and yellow fluorescence shifted from dispersed one to strong dotted ones and the locations of fluorescence for each color were same like the above and thus it was confirmed that the fluorescent proteins emitting each color were co-located (FIG. 18c).

On the other hand, when cells co-transfected with the CIBN-RFP-AD construct, the PHR-ECFP-Hras(inactive) construct and the YFP-RBD$_{raf1}$ construct (FIG. 18b) and cells co-transfected with the CIBN-RFP-AD construct, the PHR-ECFP-Hras(active) construct and the YFP-CRIB$_{PAK1}$ construct (FIG. 18d) were irradiated with blue light, patterns of red and cyan fluorescence shifted from dispersed one to strong dotted ones but patterns of yellow fluorescence had no change.

This is interpreted if there is no interaction between the bait protein and the target protein (FIG. 7). That is, nano-clusters are generated when the CIBN, a light-induced heterodimerized protein interacts with PHR-ECFP-bait protein forming a homodimer by light irradiation but the interaction between the bait protein and the target protein fails and the target protein cannot form a complex with the nano-clusters and thus the fluorescence emitted from the target protein is displayed in a dispersed pattern.

In the meanwhile, if an homodimerization is occurred between the light-induced heterodimerized protein, nano-clusters are generated regardless of light irradiation and the interaction with the partner protein is inhibited, it can be distinguished from the interaction between the light-induced heterodimerized protein and the partner protein.

As such, the method and the kit for analyzing protein-protein interaction according to various embodiments of the present invention may be useful in analyzing the interaction between different proteins excluding the possibility of false-positive and false-negative.

Experimental Example 3: Analysis of Protein Inhibition by Light Irradiation

The present inventors observed fluorescent patterns within Cos-7 cells (ATCC No. CRL-1658) co-transfected with the CIBN-mCerulean-Ad construct prepared in the example 3-1, the mCitrine-PHR$_{CRY2}$-DHPH$_{Vav2}$-Rit tail construct prepared in the example 3-4 and the mCherry-lifeact construct prepared in the example 3-5 over time after irradiating blue light having 488 nm of wavelength capable of inducing the interaction between CIBN and CRY2 using pulsed irradiation (for total 4 min with 1 sec per irradiation at an interval of 10 secs). As a result, it was confirmed that nano-clusters were generated by light irradiation from the phenomenon that strong green fluorescent dots were generated and the formation of lamellipodia was inhibited (FIG. 19). The present inventors performed similar experiment using the mCitrine-PHR$_{CRY2}$-Rit tail construct prepared in the example 1-3 instead of the mCitrine-PHR$_{CRY2}$-DHPH$_{Vav2}$-Rit tail construct prepared in example 3-4 in order to investigate whether the inhibition of lamellipodia formation is due to the capture of Vav2 protein within the nano-cluster. As a result, as shown in FIG. 19, nano-clusters were generated by light irradiation, but it was irrelevant to the formation of lamellipodia.

While the present invention has been described in connection with certain exemplary examples, it is to be understood that the invention is not limited to the disclosed examples, but, on the contrary, is intended to cover various modifications and equivalent arrangements included within the spirit and scope of the appended claims, and equivalents thereof.

INDUSTRIAL APPLICABILITY

The method for generating light-induced protein nano-clusters according to an embodiment of the present invention may be used as a useful tool for analyzing various protein-protein interaction and analyzing function of proteins by reversible inhibition of the proteins.

SEQUENCE LISTING FREE TEXT

SEQ ID NO: 1 is the amino acid sequence of the tetra-cysteine fluorescent motif.

The invention claimed is:

1. A method for forming a protein nano-cluster, wherein the method comprises:
providing a first expression vector including a polynucleotide encoding a first fusion protein comprising a light-induced heterodimerized protein and a first self-assembled protein, and a second expression vector including a polynucleotide encoding a partner protein capable of forming a heterodimer with the light-induced heterodimerized protein, or a second fusion protein containing the partner protein and a second self-assembled protein; transforming a cell, a tissue or a subject with the first expression vector and the second expression vector;
irradiating light having wavelength capable of inducing heterodimerization between the light-induced heterodimerized protein and the partner protein to the cell, the tissue or the subject; and
forming a protein nano-cluster.

2. The method according to claim 1, wherein the light-induced heterodimerized protein is CIB, CIBN, PhyB, PIF, FKF1, GIGANTEA, CRY, or PHR, and the partner protein is CRY or PHR when the light-induced heterodimerized protein is CIB or CIBN, the partner protein is PIF when the light-induced heterodimerized protein is PhyB, the partner protein is GIFANTEA when the light-induced heterodimerized protein is FKF1, the partner protein is CIB, CIBN, PhyB, PIF, FKF1, GIGANTEA, CRY, or PHR.

3. The method according to claim 1, wherein the first self-assembled protein and the second self-assembled protein is independently ferritin, virus capsid protein, ferritin-like protein, calcium/calmodulin-dependent protein kinase II alpha subunit (CaMKIIα) or DsRed.

4. The method according to claim 1, wherein at least one among the first fusion protein, the partner protein and the second fusion protein further comprises a fluorescent protein.

5. The method according to claim 4, wherein the fluorescent protein is added to N-terminus or C-terminus of the first fusion protein, the partner protein and/or the second fusion protein or the fluorescent protein is inserted between the light-induced heterodimerized protein and the first self-assembled protein or between the partner protein and the second self-assembled protein.

6. The method according to claim 4, wherein the fluorescent protein is green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

7. The method according to claim 5, wherein the fluorescent protein is green fluorescent protein (GFP), yellow fluorescent protein (YFP), red fluorescent protein (RFP), orange fluorescent protein, cyan fluorescent protein (CFP), blue fluorescent protein (BFP), or tetracysteine fluorescent motif.

\* \* \* \* \*